United States Patent
Román-Leshkov et al.

(10) Patent No.: US 10,099,979 B2
(45) Date of Patent: Oct. 16, 2018

(54) CATALYTIC METHODS FOR THE PRODUCTION OF AN ALCOHOL FROM AN ALKANE

(71) Applicant: Massachusetts Institute of Technology, Cambridge, MA (US)

(72) Inventors: Yuriy Román-Leshkov, Cambridge, MA (US); Karthik Narsimhan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/329,628

(22) PCT Filed: Nov. 11, 2016

(86) PCT No.: PCT/US2016/061699
§ 371 (c)(1),
(2) Date: Jan. 27, 2017

(87) PCT Pub. No.: WO2017/083773
PCT Pub. Date: May 18, 2017

(65) Prior Publication Data

US 2017/0267616 A1    Sep. 21, 2017

Related U.S. Application Data

(60) Provisional application No. 62/255,142, filed on Nov. 13, 2015.

(51) Int. Cl.
*C07C 29/50* (2006.01)
*C07B 41/02* (2006.01)

(52) U.S. Cl.
CPC .............. *C07C 29/50* (2013.01); *C07B 41/02* (2013.01)

(58) Field of Classification Search
CPC ................................ C07C 29/50; C07B 41/02
USPC ....................................................... 568/910
See application file for complete search history.

(56) References Cited

U.S. PATENT DOCUMENTS

| | | | |
|---|---|---|---|
| 3,702,886 | A | 11/1972 | Argauer et al. |
| 4,661,467 | A | 4/1987 | Kuehl |
| 4,665,249 | A | 5/1987 | Mao et al. |
| 5,345,011 | A | 9/1994 | Durante et al. |
| 2005/0203323 | A1 | 9/2005 | Harris et al. |
| 2007/0270512 | A1 | 11/2007 | Edwards |
| 2008/0249197 | A1 | 10/2008 | Bricker et al. |
| 2010/0280289 | A1 | 11/2010 | De Winne et al. |

FOREIGN PATENT DOCUMENTS

WO    WO 2011/046621 A1    4/2011

OTHER PUBLICATIONS

International Search Report and Written Opinion for Application No. PCT/US16/61699 dated Feb. 15, 2017.
Narsimhan et al., Methane to Acetic Acid over Cu-Exchanged Zeolites: Mechanistic Insights from a Site-specific Carbonylation Reaction. Journal of the American Chemical Society. Feb. 2015;137(5):1825-32. Supporting Information Included.
Woertink et al., A $[Cu_2O]^{2+}$ core in Cu-ZSM-5, the active site in the oxidation of methane to methanol. Proceedings of the National Academy of Sciences of the United States of America. Nov. 2009;106(45):18908-13.
Alayon et al., Catalytic conversion of methane to methanol over Cu-mordenite. Chemical Communications. 2012;48:404-6. Epub Nov. 11, 2011.
Alayon et al., Reaction Conditions of Methane-to-Methanol Conversion Affect the Structure of Active Copper Sites. ACS Catalysis. 2014;4(1):16-22. Epub Nov. 20, 2013.
Balasubramanian et al., Oxidation of methane by a biological dicopper centre. Nature. May 6, 2010;465:115-9. Epub Apr. 21, 2010.
Behrens et al., Active Site of Methanol Synthesis over $Cu/ZnO/Al_2O_3$ Industrial Catalysts. Science. May 18, 2012;336(6083):893-7.
Blaszkowski et al., The Mechanism of Dimethyl Ether Formation from Methanol Catalyzed by Zeolitic Protons. J. Am. Chem. Soc. 1996;118:5152-3. Epub May 29, 1996.
Caballero et al., Silver-Catalyzed C—C Bond Formation Between Methane and Ethyl Diazoacetate in Supercritical $CO_2$. Science. May 13, 2011;332(6031):835-8.
Camblor et al., Spontaneous nucleation and growth of pure silica zeolite-β free of connectivity defects. Chem. Commun. 1996;20:2365-6.
Cavaliere et al., Methane: a new frontier in organometallic chemistry. Chemical Science. 2012;3:3356-65. Epub Jul. 6, 2012.
Chang et al., Methanol conversion to olefins over ZSM-5: I. Effect of temperature and zeolite $SiO_2Al_2O_3$. Journal of Catalysis. Apr. 1984;86(2):289-96.
Chang et al., Process Studies on the Conversion of Methanol to Gasoline. Ind. Eng. Chem. Process Des. Dev. Jul. 1978;17(3):255-60.
Chen et al., Spatial confinement effects of cage-type SAPO molecular sieves on product distribution and coke formation in methanol-to-olefin reaction. Catalysis Communications. Feb. 10, 2014;46:36-40.
Dejaifve et al., Reaction pathways for the conversion of methanol and olefins on H-ZSM-5 zeolite. Journal of Catalysis. Jun. 1980;63(2):331-45.
Ellis et al., Heterogeneous catalysts for the direct, halide-free carbonylation of methanol. Stud. Surf. Sci. Catal. 1996;101:771-9. Epub Oct. 14, 2008.
Gao et al., Understanding ammonia selective catalytic reduction kinetics over Cu/SSZ-13 from motion of the Cu ions. Journal of Catalysis. Nov. 2014;319:1-14. Epub Sep. 6, 2014.
Golisz et al., Chemistry in the Center for Catalytic Hydrocarbon Functionalization: An Energy Frontier Research Center. Catal Lett. Feb. 2011;141:213-21.
Gonçalves et al., Promoting Effect of Ce on the Oxidative Coupling of Methane Catalysts. Catalysis Letters. Mar. 2010;135(1-2):26-32.

(Continued)

*Primary Examiner* — Sikarl A Witherspoon
(74) *Attorney, Agent, or Firm* — Wolf, Greenfield & Sacks, P.C.

(57) ABSTRACT

The present invention generally relates to apparatuses, systems, and methods for oxidation of an alkane (e.g., methane) into an alcohol (e.g., methanol) in the presence of a catalyst.

27 Claims, 4 Drawing Sheets

(56) References Cited

OTHER PUBLICATIONS

Groothaert et al., Selective Oxidation of Methane by the Bis(μ-oxo)dicopper Core Stabilized on ZSM-5 and Mordenite Zeolites. J. Am. Chem. Soc. 2005;127(5):1394-5. Epub Jan. 15, 2005.
Grundner et al., Single-site trinuclear copper oxygen clusters in mordenite for selective conversion of methane to methanol. Nature Communications. 2015;6:7546. Epub Jun. 25, 2015. 9 pages.
Grundner et al., Synthesis of single-site copper catalysts for methane partial oxidation. Chem Commun. 2016;52:2553-6. Epub Dec. 24, 2015.
Hammond et al., Direct Catalytic Conversion of Methane to Methanol in an Aqueous Medium by using Copper-Promoted Fe-ZSM-5. Angewandte Chemie Int Ed. May 21, 2012;51(21):5129-33.
Hammond et al., Elucidation and Evolution of the Active Component within Cu/Fe/ZSM-5 for Catalytic Methane Oxidation: From Synthesis to Catalysis. ACS Catalysis. 2013;3(4):689-99. Epub Feb. 7, 2013.
Hammond et al., Oxidative Methane Upgrading. ChemSusChem. Sep. 2012;5(9):1668-86.
Hassanpour et al., Performance of modified H-ZSM-5 zeolite for dehydration of methanol to dimethyl ether. Fuel Processing Technology. Oct. 2010;91(10):1212-21.
Ito et al., Synthesis of ethylene and ethane by partial oxidation of methane over lithium-doped magnesium oxide. Nature. Apr. 25, 1985;314:721-2.
Khalilpour et al., Evaluation of utilization alternatives for stranded natural gas. Energy. Apr. 2012;40(1):317-28.
Kopp et al., Soluble methane monooxygenase: activation of dioxygen and methane. Current Opinion in Chemical Biology. Oct. 1, 2002;6(5):568-76.
Lee et al., Structural and Functional Models of the Dioxygen-Activating Centers of Non-Heme Diiron Enzymes Ribonucleotide Reductase and Soluble Methane Monooxygenase. J. Am. Chem. Soc. 1998;120(46):12153-4. Epub Nov. 10, 1998.
Li et al., Hydrated Dibromodioxomolybdenum(VI) Supported on Zn-MCM-48 for Facile Oxidation of Methane. Angewandte Chemie Int Ed. 2006;45:6541-4. Epub Sep. 5, 2006.
Li et al., Stability and reactivity of copper oxo-clusters in ZSM-5 zeolite for selective methane oxidation to methanol. Journal of Catalysis. Jun. 2016;338:305-12.
Lieberman et al., Crystal structure of a membrane-bound metalloenzyme that catalyses the biological oxidation of methane. Nature. Mar. 10, 2005;434:177-82. Epub Jan. 26, 2005.
Lunsford, Catalytic conversion of methane to more useful chemicals and fuels: a challenge for the 21st century. Catalysis Today. Dec. 25, 2000;63(2-4):165-74.
Martínez-Franco et al., Rational direct synthesis methodology of very active and hydrothermally stable Cu-SAPO-34 molecular sieves for the SCR of $NO_x$. Applied Catalysis B: Environmental. Oct. 30, 2012;127:273-80.
Narsimhan et al., Catalytic Oxidation of Methane into Methanol over Copper-Exchanged Zeolites with Oxygen at Low Temperature. ACS Cent. Sci. 2016;2(6):424-9. Epub Jun. 13, 2016. Supporting Information Included.
Ovanesyan et al., The state of iron in the Fe-ZSM-5-N2O system for selective oxidation of methane to methanol from data of Mössbauer spectroscopy. Kinet. Catal. 1998;39:792-7.
Palkovits et al., Solid Catalysts for the Selective Low-Temperature Oxidation of Methane to Methanol. Angewandte Chemie Int Ed. Sep. 1, 2009;48(37):6909-12.
Palomino et al., Oxidation States of Copper Ions in ZSM-5 Zeolites. A Multitechnique Investigation. J. Phys. Chem. B. 2000;104(17):4064-73. Epub Mar. 30, 2000.
Panov et al., Iron complexes in zeolites as a new model of methane monooxygenase. Reaction Kinetics and Catalysis Letters. Jul. 1997;61(2):251-8.
Periana et al., A Mercury-Catalyzed, High-Yield System for the Oxidation of Methane to Methanol. Science. Jan. 15, 1993;259(5093):340-3.
Periana et al., Platinum Catalysts for the High-Yield Oxidation of Methane to a Methanol Derivative. Apr. 24, 1998;280(5363):560-4.
Persson et al., The synthesis of discrete colloidal particles of TPA-silicalite-1. Zeolites. Sep.-Oct. 1994;14(7):557-67.
Ren et al., Designed copper-amine complex as an efficient template for one-pot synthesis of Cu-SSZ-13 zeolite with excellent activity for selective catalytic reduction of $No_x$ by $NH_3$. Chemical Communications. 2011;47:9789-91. Epub May 31, 2011.
Sajith et al., Role of Acidic Proton in the Decomposition of NO over Dimeric Cu(I) Active Sites in Cu-ZSM-5 Catalyst: a QM/MM Study. ACS Catalysis. 2014;4(6):2075-85. Epub May 15, 2014.
Shu et al., an $Fe_2^{IV}O_2$ Diamond Core Structure for the Key Intermediate Q of Methane Monooxygenase. Science. Jan. 24, 1997;275(5299):515-8.
Smeets et al., Cu based zeolites: A UV—vis study of the active site in the selective methane oxidation at low temperatures. Catalysis Today. Dec. 30, 2005;110(3-4):303-9.
Smith et al., Catalytic borylation of methane. Science. Mar. 25, 2016;351(6280):1424-7.
Song et al., A high performance oxygen storage material for chemical looping processes with $CO_2$ capture. Energy Environ. Sci. 2013;6:288-98. Epub Nov. 22, 2012.
Sunley et al., High productivity methanol carbonylation catalysis using iridium: The Cativa™ process for the manufacture of acetic acid. Catalysis Today. May 26, 2000;58(4):293-307.
Thomas et al., Review of ways to transport natural gas energy from countries which do not need the gas for domestic use. Energy. Nov. 2003;28(14):1461-77.
Tomkins et al., Isothermal Cyclic Conversion of Methane into Methanol over Copper-Exchanged Zeolite at Low Temperature. Angewandte Chemie Int Ed. 2016;55:5467-71. Epub Mar. 24, 2016.
Unruh et al., Fischer-Tropsch Synfuels from Biomass: Maximizing Carbon Efficiency and Hydrocarbon Yield. Energy Fuels. 2010;24(4):2634-41. Epub Mar. 30, 2010.
Vanelderen et al., Cu-ZSM-5: A biomimetic inorganic model for methane oxidation. Journal of Catalysis. Dec. 1, 2011;284(2):157-64.
Vanelderen et al., Spectroscopic Definition of the Copper Active Sites in Mordenite: Selective Methane Oxidation. J. Am. Chem. Soc. 2015;137(19):6383-92. Epub Apr. 26, 2015.
Vishwanathan et al., Vapour phase dehydration of crude methanol to dimethyl ether over Na-modified H-ZSM-5 catalysts. Applied Catalysis A: General. Nov. 25, 2004;276(1-2):251-5.
Wang et al., Role of Surface Methoxy Species in the Conversion of Methanol to Dimethyl Ether on Acidic Zeolites Investigated by in Situ Stopped-Flow MAS NMR Spectroscopy. J. Phys. Chem. B. 2001;105(50):12553-8. Epub Nov. 21, 2001.
Wulfers et al., Conversion of methane to methanol on copper-containing small-pore zeolites and zeotypes. Chem. Comm. 2015;21:4447-50. Epub Feb. 4, 2015.
Yaripour et al., Catalytic dehydration of methanol to dimethyl ether (DME) over solid-acid catalysts. Catalysis Communications. Feb. 2005;6(2):147-52.

CATALYTIC METHODS FOR THE PRODUCTION OF AN ALCOHOL FROM AN ALKANE

RELATED APPLICATIONS

This application is a national stage application under 35 U.S.C. § 371 of International Patent Application Serial No. PCT/US2016/061699, filed on Nov. 11, 2016, entitled "CATALYTIC METHODS FOR THE PRODUCTION OF AN ALCOHOL FROM AN ALKANE," which claims priority to U.S. Provisional Patent Application Ser. No. 62/255,142, filed Nov. 13, 2015, entitled, "CATALYTIC, LOW TEMPERATURE, VAPOR PHASE OXIDATION OF METHANE INTO METHANOL," each of which is herein incorporated by reference in its entirety for all purposes.

FIELD OF THE INVENTION

The present invention generally relates to apparatuses, systems, and methods for oxidation of an alkane into an alcohol.

BACKGROUND OF THE INVENTION

Different strategies have been used to convert an alkane species into alcohol. For example, a common strategy to convert methane into higher valued fuels is the gas-to-liquids (GTL) process of steam reforming methane into syngas (CO and $H_2$) and subsequent reaction into methanol, but GTL requires large scales and billions in capital investment. This industrial pathway to convert methane into methanol involves two capital-intensive reactions: steam reforming and methanol synthesis. Steam reforming converts methane and water into hydrogen and carbon monoxide gases. This "syngas" is then fed into a methanol synthesis unit where the syngas is converted into methanol or other hydrocarbons. Several drawbacks exist for this industrial pathway. Firstly, the technical complexity is high. Two reaction units must be built as well as associated separations units afterwards. Numerous cryogenic separations and other utilities are needed to purify the syngas effluent from steam reforming to allow methanol synthesis to proceed efficiently. Auxiliary operations within the gas-to-liquids plants accounts for roughly half of the plant cost. Such technical complexity requires extremely large scale production facilities, thereby incurring high capital costs for gas-to-liquids plants. Secondly, steam reforming is energy intensive due to the high temperatures required (greater than 800° C.). Lastly, methanol synthesis requires high pressures (50-100 bar), incurring additional cost for compression pumps.

To avoid the large scale production facilities needed to make steam reforming and methanol synthesis profitable, alternatives have been researched for the direct partial oxidation of methane. One proposed alternative has been to utilize enzymes. An inherent problem with using enzymes industrially is their sensitivity to harsh temperatures and pH, difficulty of purifying large amounts of homogeneous enzyme, and difficulty in purification of alcohol products and enzyme from liquid water (solvent).

Inorganic catalysts for methane oxidation have been developed, but all suffer from at least one of the following deficiencies: expensive catalyst or oxidant, low selectivity, high temperatures, economic and/or energy inefficiency, or environmentally harmful reagents needed. Copper exchanged zeolites ZSM-5 and mordenite (MOR) have been studied for use in oxidizing methane at low temperatures (less than 423 K) using molecular oxygen. Yet, oxidized methane is strongly bound to the copper active site or Bronsted acid sites as a surface methoxy species, requiring water to extract methanol while simultaneously deactivating the active sites. Therefore, conversion of methane to methanol utilizing inorganic catalysts (e.g., zeolites) has heretofore been done stoichiometrically—with the production of methanol limited by the number of active sites for one cycle without the ability to sustain a continuous reaction process. Such a process would generally proceed as follows. The catalysts would be activated at a higher temperature. A flow of pure methane at a lower temperature would produce methoxy species at the active sites of the catalyst. Once the active sites of catalyst material were occupied by an oxidized methane molecule, an atmosphere of water would be introduced to extract this methoxy species as methanol. The deactivated catalyst would be dried and then heated to high temperatures to reactivate the catalyst. The multi-step cycle would then be repeated in order to extract a second set of stoichiometrically produced methanol. Such a process results in energy losses and lost time of unutilized catalyst during regeneration.

Accordingly, methods for catalytic alcohol (e.g., methanol) production are needed.

SUMMARY OF THE INVENTION

The present invention generally relates to apparatuses, systems, and methods for oxidation of an alkane into an alcohol.

According to one or more embodiments, a method of catalytically forming an alcohol from an alkane is described. The method may comprise exposing a catalyst to an atmosphere comprising the alkane, an oxidizing agent, and a protic solvent, wherein alcohol is formed by conversion of the alkane, the oxidizing agent, and the protic solvent.

According to one or more embodiments, a method of catalytically forming methanol from methane is described. The method may comprise exposing a catalyst to an atmosphere comprising methane, oxygen, and water, wherein methanol is formed by conversion of methane, oxygen, and water.

According to one or more embodiments, a method of catalytically forming methanol from methane is described. The method may comprise exposing a catalyst to methane, oxygen, and water, wherein methanol is formed by conversion of methane, oxygen, and water at a steady state production rate of from about 0.5 to about 160 μmol per hour per gram of catalyst.

Figure 1:
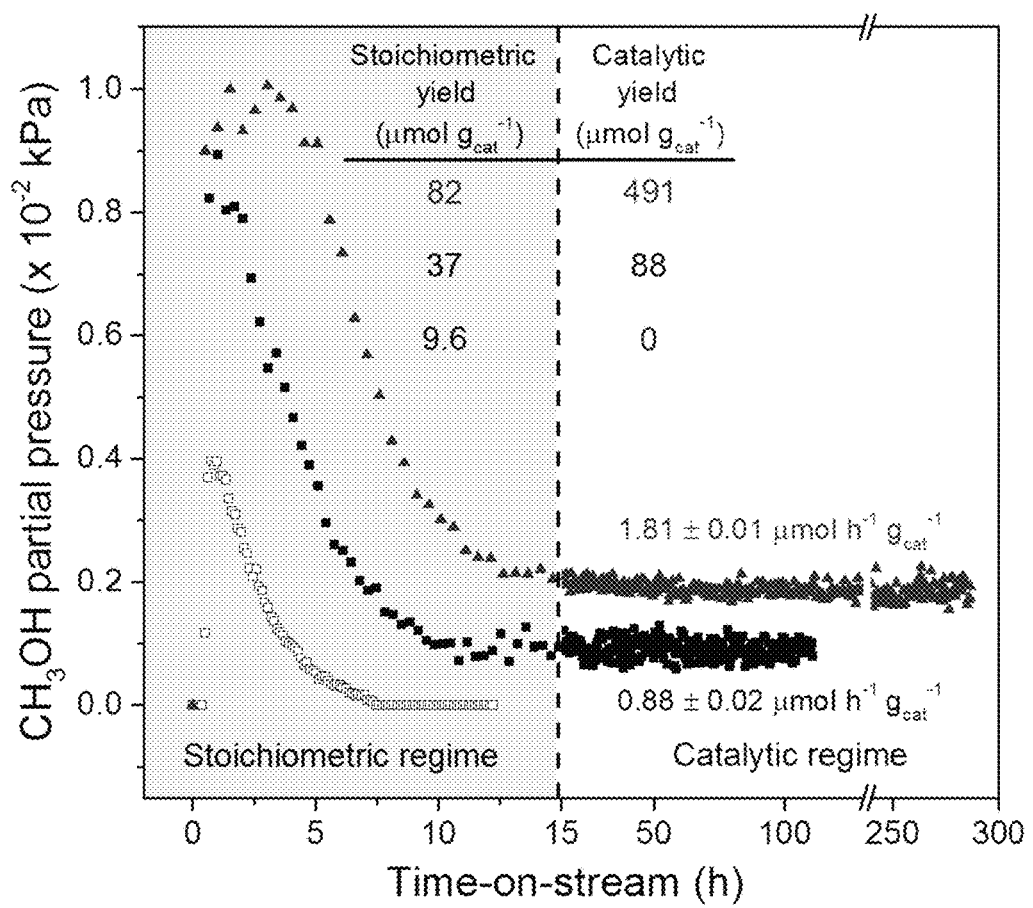
FIG. 1 is a graphical representation of methanol production, according to one or more non-limiting embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present disclosure generally relates to apparatuses, systems, and methods for oxidation of an alkane (e.g., methane) into an alcohol (e.g., methanol).

According to some embodiments, methods of catalytically forming an alcohol from an alkane are generally described. The method may comprise exposing a catalyst to an atmosphere comprising the alkane, an oxidizing agent, and a protic solvent, wherein alcohol is formed by conversion (e.g., direct conversion) of the alkane, the oxidizing agent, and the protic solvent. In a specific example, methods of catalytically forming methanol from methane are generally described. The method may comprise exposing a catalyst to an atmosphere comprising methane, oxygen, and water, wherein methanol is formed by conversion (e.g., direct conversion) of methane, oxygen, and water.

Without being bound to a particular theory, it is believed that the continuous and/or catalytic nature of the methods described herein are achieved through proper choice of catalyst and/or the proper combination of components in the atmosphere surrounding the catalyst during alcohol production. The inventors unexpectedly discovered that use of a combination of alkane, oxidizing agent, and protic solvent (e.g., methane, oxygen and water) in the presence of a wide range of catalysts lead to continuous, catalytic production of alcohol (e.g., methanol). More specifically, the process described herein resulted in a certain number of active sites which were unexpectedly found to be tolerant to the oxidizing agent and solvent, and could therefore continuously operate without having to be separately reactivated, ultimately producing more methanol than the total number of active sites present in the catalyst. Such a continuous operation may be contrasted with previous stoichiometric methods for producing methanol with use of an inorganic catalyst would result in one or less than one molecule per active site in the catalyst, and in which the extraction process would deactivate sites of the catalyst, requiring the production process to be stopped to reactivate the catalyst at high temperature.

A catalytic process is provided which allows for the direct conversion of alkane (e.g., methane) into alcohol (e.g., methanol) in the gas phase in the presence of a catalyst. According to some embodiments, processes generally described herein allow for the production of alcohol to take place according to a catalytic process, in contrast to known stoichiometric processes. Such catalytic processes may allow for the production of an amount of alcohol (e.g., methanol) that exceeds the number of active sites in the catalyst for a given production cycle.

The phrase "catalytic process" is given its ordinary meaning in the art and generally refers to a continuous process wherein on average, more than one molecule of product is produced per a single active site of the catalyst. For example, a catalytic process does not include the regeneration of the catalyst through a separate regeneration process. The phrase "stoichiometric process" is given its ordinary meaning in the art and generally refers to a process in which only one molecule of product is produced per a single active site of the catalyst, wherein the active site is inactive following formation of the molecule of product. Thus, in contrast to a catalytic process, in order to produce more than one molecule of product per a single active site of the catalyst, the catalyst must be regenerated through a separate regeneration process. In some embodiments, in which the precise number of active sites has not been fully determined, but has been limited to a particular class, such as moles of a particular metal (for example, copper), the total number of moles of that metal serve as a ceiling to the number of possible active sites. According to such embodiments, a process is catalytic where the moles of product generated exceed the moles of that metal (e.g., copper), without requiring a separate regeneration process.

According to one or more embodiments, the alkane and the alcohol may be represented by the general formulae, $R^1CH_3$ and $R^1CH_2OH$, respectively, where $R^1$ is hydrogen or an optionally substituted alkyl group. In some embodiments, $R^1$ is unsubstituted alkyl. In embodiments where methane is converted to methanol, $R^1$ is H.

According to some embodiments the atmosphere comprises a protic solvent. The term solvent is given its ordinary meaning in the art and refers to a substance capable of desolving a solute (a chemically distinct liquid, solid or gas), resulting in a solution. A solvent is usually a liquid but can also be a solid or a gas. The term protic solvent is given its ordinary meaning in the art and generally refers to a solvent that comprises a labile $H^+$. For example, protic solvents readily donate protons ($H^+$) to reagents. In some embodiments, the protic solvent has a hydrogen atom bound to an oxygen (as in a hydroxyl group) or a nitrogen (as in an amine group). Non-limiting examples of protic solvents include water, alcohols (e.g., ethanol), formic acid or any inorganic acid, such as HCl or nitric acid. In some embodiments, the protic solvent is water. In some embodiments, the protic solvent is ethanol. Alternative or additional protic solvents or a combination of protic solvents or a combination of protic and aprotic solvents (e.g., a combination of water and an aprotic solvent, such as, acetonitrile) may be used, in some embodiments.

According to some embodiments, the atmosphere comprises an oxidizing agent. The term oxidizing agent is given its ordinary meaning in the art and generally refers to a reactant that has the ability to oxidize or increase the oxidation state of another reactant. In the processes described herein, generally the oxidizing agent serves as a source of oxygen for the reaction to convert the alkane species to the alcohol species. Non-limiting examples of oxidizing agents include oxygen ($O_2$), ozone ($O_3$) nitric oxide, nitrous oxide, and hydrogen peroxide. In some embodiments, the oxidizing agent is oxygen ($O_2$). Alternative or additional oxidizing agents or a combination of oxidizing agents may be used, in some embodiments.

While reference will often be made to methane, water, oxygen, and methanol, in describing embodiments of the disclosure, herein, it should be understood that other alkanes, protic solvents, oxidizing agents, and alcohols, respectively, could be substituted for those particular species, unless otherwise noted.

Those of ordinary skill in the art will be aware of systems and methods for exposing a catalyst to an atmosphere comprising an alkane, oxidizing agent and protic solvent. Generally, the alkane, oxidizing agent and protic solvent are in the gaseous stage, and the reaction is carried out in an apparatus suitable for gaseous reaction. In some embodiments, the reaction is carried out in a reactor (e.g., a packed bed reactor) in which the catalyst is exposed to the alkane, oxidizing agent and protic solvent in a gaseous stream that is introduced to the reactor. The different components of the atmosphere may be introduced to the reactor from a single inlet or from multiple inlets. The gas stream may be introduced to the reactor continuously, for example, when the reactor is operating in a continuous mode, and a continuous reaction is taking place. According to some embodiments, the atmosphere may comprise an atmosphere of a sealed reactor, in which no new matter enters or exits the reactor during operation in a batch mode.

According to one or more embodiments, the catalyst is exposed to the alkane, the oxidizing agent, and the protic solvent simultaneously. By simultaneous it is meant that the different components are in the proximity of the catalyst at the same time, for example, as components in a gas mixture. For example, the catalyst is exposed to a continuous gaseous stream comprising the alkane, the oxidizing agent, and the protic solvent (e.g., as opposed to a stream comprising first the alkane and the oxidizing agent, following by a stream at a different point in time comprising the protic solvent).

According to one or more embodiments, the alcohol (e.g., methanol) is formed by direct conversion of alkane, an oxidizing agent, and a protic solvent (e.g., methane, oxygen, and water, respectively). As used herein the phrase "direct conversion" refers to a conversion of reactants to product which takes place in a reactor, into which the reactants are introduced and from which the product(s) forms under a single set of process conditions (e.g., over the same or substantially same temperature and pressure, and in the presence of a single feedstock). For example, a catalyst is exposed to a gaseous stream comprising all of the reactants under a first set of conditions (e.g., temperature, pressure, components of gaseous stream, etc.) and the product is formed without a change in the first set of conditions. Such direct conversion may be distinguished from conversion mechanisms in which multiple unit operations are required to convert the alcohol, for example, conversion mechanisms that comprise both steam reforming and methanol synthesis.

According to one or more embodiments, prior to the exposing step, the catalyst may be activated. In some embodiments, the catalyst may be activated under a flow of oxygen. The concentration of oxygen by volume may vary widely. In some embodiments, the flow of oxygen ($O_2$) may comprise at least 80%, at least 90%, or at least 99% oxygen by volume. In some embodiments, the flow of oxygen ($O_2$) during activation may be less than 0.01% oxygen by volume.

In embodiments where an activation step takes place, the step of activating the catalyst may be carried out at a particular temperature or temperature range. The temperature during activation may be greater than the temperature during the exposing step. For example, the activation step may be carried out at a temperature of about 450° C., or between about 450° C. and about 700° C., or between about 450° C. and about 600° C., or between about 450° C. and about 550° C., or between about 500° C. and about 700° C., or between about 500° C. and about 600° C.

The activation step may be performed for a certain length of time. In some embodiments activation may take place for between about 1 to 10 hours, or between about 4 to 6 hours.

According to some embodiments, after activation, a flow of inert gas (e.g., He, Ar, $N_2$) may be introduced to the environment surrounding the catalyst to purge any remaining oxygen. According to some embodiments, the purging may take place for a period of from about ten minutes to two hours.

Following activation, the temperature of the catalyst may be lowered to a temperature at which the exposure of the catalyst to the protic solvent, alkane, and oxidizing agent is carried out.

The step of exposing the catalysts to the alkane species, the oxidizing agent, and the protic solvent may be carried out at a designated temperature or temperature range. According to some embodiments the exposing is carried out at a temperature between about 60° C. to about 500° C., between about 190° C. and about 400° C., between about 200° C. and about 400° C., or between about 200° C. and about 260° C.

The methanol production described herein may take place at generally higher temperatures than previous stoichiometric techniques, in which at temperatures higher than about 200° C. the methoxy groups are over-oxidized to create $CO_2$ rather than methanol.

According to some embodiments, a flow of methane may optionally be introduced to the catalyst prior to exposing the catalyst to an atmosphere comprising a mixture of methane, oxygen, and water. This optional flow of methane may comprise at least 90% methane, at least 95% methane, or at least 99% methane by volume. In some embodiments the optional flow of methane may be at least 10%, or at least 40% by volume. Other concentrations are also possible. The methane may be introduced for a period of time. In some embodiments the flow of pure methane may be introduced for a period of about ten minutes to an hour. During this period, a portion of the methane stream may form methoxy or methanol groups at active sites of the catalyst. Alternatively, the step of flowing a pure or substantially pure stream of methane to stoichiometrically form methanol may be bypassed.

After this period of introducing a methane stream, water and oxygen may be added to the stream to simultaneously expose the catalyst to an atmosphere comprising water, oxygen, and methane. The methoxy or methanol groups stoichiometrically formed during the flow of pure methane are then extracted as methanol, while the flow continues to generate additional methanol, catalytically.

According to one or more embodiments, the atmosphere surrounding the catalyst may have a particular pressure during the step of exposing a catalyst to an atmosphere comprising the alkane, an oxidizing agent, and a protic solvent. For example, the atmosphere may have a pressure of or substantially near to atmospheric pressure. In some embodiments, the pressure may be at least about 0.8, 0.9, 1.0, 1.1 or 1.2 ATM. In some embodiments, the pressure may be less than or equal to about 1.3, 1.2, 1.1, 1.0, or 0.9 ATM. Combinations of the above values are also possible (e.g., a pressure of at least about 0.8 ATM and less than or equal to about 1.2 ATM. Other pressures are also possible; for example, in some embodiments the pressure may be at least 0.1 ATM, while in other embodiments the pressure may be at least or about 5 ATM, 10 ATM, 15 ATM, 50 ATM or 80 ATM.

According to one or more embodiments, the atmosphere may comprise alkane species, the oxidizing agent, and the protic solvent according to designated proportions. For example, in embodiments in which the atmosphere comprises water, oxygen, and methane, these constituents may be present at certain proportions. In some embodiments, the concentrations of the different components may be chosen to maximize alcohol (e.g., methanol) production. Without being bound to a particular theory, it is believed that the reaction rate for methanol production is zero order with respect to oxygen. Accordingly, the concentration of oxygen may be chosen to be enough to saturate the active sites of the catalyst with the understanding that any concentration above that amount is not contributing to the reaction rate. Without being bound to a particular theory, it is believed that the reaction rate for methanol production is half order with respect to water. Accordingly, as the concentration of water increases so does the production rate. However, raising the partial pressure of water in the atmosphere would at some point become detrimental as its presence limits the amount of methane that may be present in the mixture. Methane may make up the balance of the atmosphere. Without being bound to a particular theory, it is believed that the production rate of methanol is proportional to the concentration of methane in the atmosphere.

According to some embodiments, during the exposing step, water may be present at a concentration by volume of from about 1,000 ppm to about 50,000 ppm, from about 10,000 ppm to about 40,000 ppm, or from about 20,000 ppm to about 35,000 ppm (or a partial pressure of from about 0.1 kPa to about 5 kPa, from about 1 kPa to about 4 kPa, or from about 2 kPa to about 3.5 kPa, where pressure is atmospheric) or greater during the exposing step; oxygen ($O_2$) may be present at a concentration by volume of from about 5 ppm to about 1000 ppm, from about 10 ppm to about 500 ppm, or from about 20 ppm to about 100 ppm (or at a partial pressure of from about 0.0005 kPa to about 0.1 kPa, from about 0.001 kPa to about 0.05 kPa, or from about 0.002 kPa to about 0.01 kPa, where pressure is atmospheric) or greater during the exposing step; and the balance may be methane, where ppm refers to parts per million by volume. In some embodiments methane may be present at a concentration of at least about 30%, 50%, 80%, or 90% by volume (or at a partial pressure from at least about 90 kPa where pressure is atmospheric). In some embodiments incorporating a different protic solvent, oxidizing agent, and or alkane than water, oxygen, and methane, respectively, similar concentrations may still apply.

According to one or more embodiments, the production of alcohol is determined once the reaction has reached a steady state (e.g., the steady state production rate). The term steady state is given its ordinary meaning in the art and generally refers to embodiments wherein all of the variables of a reaction and/or system are substantially constant for a period of time, for example, when the production of methanol, the variables temperature, the pressure, the ratio of components in the feedstock, etc., are substantially constant. In such embodiments, the steady state production rate is the rate in which methanol is produced under the steady state conditions. In other words, the steady state production rate refers to embodiments wherein for a period of time the system is under steady state conditions and the production rate of methanol remains substantially constant (e.g., varies by less than 20%, or less than 10%, or less than 5%, at any given time over the steady state period average). Those of ordinary skill in the art will be aware of methods for determining the steady state production rate, for example, by plotting the rate of methanol production via time and determining the rate once the plot has leveled (e.g. varies by less than 20%, or 10%, or 5%). For example, as shown in FIG. 1, which shows non-limiting experimental results of methanol production, steady state methanol production over Cu—Na-ZSM-5 catalyst is achieved at about 15 hours (shown on the right side of the figure and labelled "catalytic regime") where a steady state production rate methanol is maintained for the duration of operation. In some embodiments, the steady state production rate of alcohol varies by no more than 1%, or 2%, or 3%, or 5%, or 10%, or 15%, or 20%, over a period of 1 day, or 2 days, or 3 days, or 4 days, or 5 days.

According to some embodiments, the method may comprise exposing a catalyst to alkane (e.g., methane), oxygen, and water, wherein the alcohol (e.g., methanol) is formed by conversion of alkane (e.g., methane), oxygen, and water at a particular steady state production rate. In some embodiments there is a steady state production rate of alcohol (e.g., methanol) of at least 0.1, 0.5, 1, 2.5, 5, 10, 20, 50, 100, 130 or 160 µmol per hour per gram of catalyst. In some embodiments, ranges comprising the above values are also possible (e.g., a steady state production rate of alcohol (e.g., methanol) of from about 0.5 to about 2.5, or of from about 100 to about 160, or of from about 0.5 to about 160 µmol per hour per gram of catalyst). Other rates are also possible.

During the period in which the catalyst is exposed to the alkane species, the oxidizing agent, and the protic solvent, a steady state production rate of alcohol (e.g., methanol) may take place. In some embodiments, steady state production rate of alcohol (e.g., methanol) varies by no more than 1%, or 2%, or 3%, or 5%, or 10%, or 15%, or 20%, over a period of 1 day, or 2 days, or 3 days, or 4 days, or 5 days, or 10 days, or 12 days, or 15 days, or 1 month, or 2 months, or 3 months, or 6 months, or 1 year.

In some embodiments, the catalytic reaction is highly selective for the production of methanol. For example, in some embodiments, the selectivity of the reaction for methanol is at least 50%, or at least 60%, or at least 65%, or at least 70%, or at least 75%, or at least 80%, or at least 85%, or at least 90%, or at least 95%. As used herein, the term selectivity is given its ordinary meaning and generally refers to the moles of carbon in alcohol (e.g., methanol) produced divided by the total moles of carbon produced for all products.

According to certain embodiments, the catalytic process may result in a particular turnover frequency, the number of chemical conversions of substrate molecules (i.e., alkane species) per second at a catalytic active site. Those of ordinary skill in the art will be aware of methods to determine an approximate number of active sites for the catalyst. In some embodiments, the number of active sites, or at least a theoretical ceiling to the number of active sites, may be determined by determining the number of moles of copper (or other exchanged metal) in the catalyst. According to certain embodiment, the turnover frequency may be from about $1\times10^{-2}$ $s^{-1}$ to about $1\times10^{-6}$ $s^{-1}$, from about $1\times10^{-3}$ $s^{-1}$ to about $10^{-5}$ $s^{-1}$, or from about $1\times10^{-4}$ $s^{-1}$ to about $1\times10^{-5}$ $s^{-1}$. Other turnover frequencies are also possible.

According to certain embodiments, the catalytic process may result in a particular site time yield. The term "site time yield" is given its ordinary meaning in the art and generally refers to the number of molecules of a specified product (e.g., methanol) made per active site per unit of time. According to certain embodiments, the site time yield may be at least $1\times10^{-3}$, $2\times10^{-3}$, $4\times10^{-3}$, $6\times10^{-3}$, $8\times10^{-3}$, $1\times10^{-2}$, 0.1, 1, 2, or 3 mol alcohol (e.g., $CH_3OH$) per mol active site per hour. According to certain embodiments, the site time yield may be less than 5, 3, 2, 1, 0.1, $1\times10^{-2}$, $8\times10^{-3}$, $6\times10^{-3}$, $4\times10^{-3}$, or $2\times10^{-3}$ mol alcohol (e.g., $CH_3OH$) per mol active site per hour. Combinations of the above ranges are also possible, for example, at least $6\times10^{-3}$ and less than $10\times10^{-3}$ mol alcohol (e.g., $CH_3OH$) per mol active site per hour. Other values are also possible.

According to certain embodiments, the catalytic process may have a particular specific activity. The term specific activity is given its ordinary meaning in the art and generally refers to the rate of alcohol production and may be expressed in units of μmol of alcohol (e.g. $CH_3OH$) per hour per gram of catalyst. In some embodiments, the specific activity for alcohol production may be at least 0.3, 0.5, 1.0, 1.5, 2.0, 2.5, 3, 10, 50, 100, 150 μmol of alcohol (e.g. $CH_3OH$) per hour per gram of catalyst. In some embodiments, the specific activity for alcohol production may be less than or equal to 175, 150, 100, 50, 10, 3.5, 3, 2.5, or 2.0 μmol of alcohol (e.g. $CH_3OH$) per hour per gram of catalyst. Combinations of the above values are also possible, for example the specific activity for alcohol production may be at least 2 and less than or equal to 4 μmol of alcohol (e.g. $CH_3OH$) per hour per gram of catalyst. Other values are also possible.

According to some embodiments, the number of moles of methanol generated for the duration of steady state operation may exceed the number of moles of active sites on the catalyst. According to some embodiments, the number of moles of methanol generated for the duration of steady state operation may exceed the number of moles of counter cation (e.g., copper) in the catalyst. According to some embodiments, ratio of moles of alcohol produced at steady state to the moles of active sites (measured as moles of copper or other exchanged metal) is at least 1.1, at least 1.4, at least 2, at least 3, at least 5, at least 10, at least 50, at least 100, at least 150, at least 200, at least 250, or at least 300. Other values are also possible.

The catalyst used may be selected from a variety of catalysts, including commercially available catalysts. According to one or more embodiments, the catalyst may comprise a zeolite. The term zeolite generally refers to a crystalline porous material having a framework of oxides comprising silicon and, optionally, aluminum and/or one or more additional elements (e.g., boron, gallium, and/or phosphorous). According to some embodiments, the zeolite comprises a silicate framework. According to some embodiments, the zeolite comprises a aluminosilicate framework. According to some embodiments, the zeolite comprises a silicoaluminophosphate framework. According to some embodiments, the zeolite comprises framework comprising a trivalent metal. According to some embodiments, the zeolite comprises a borosilicate framework. According to some embodiments, the zeolite comprises a gallosilicate framework. According to some embodiments, the zeolite comprises a zincosilicate framework.

Examples of zeolites that may be used as a framework of the catalyst include ZSM-5, mordenite (MOR), ferrierite (FER), beta (BEA), chabazite (CHA), and mobil composition of matter (MCM). Other commercially or non-commercially available zeolites may also be implemented.

According to one or more embodiments, a framework of the catalyst may be charged (e.g., negatively charged). For example, in some embodiments, aluminum in the zeolite creates a charge imbalance that is compensated for by a counter cation (e.g., copper). The framework of the catalyst (e.g., zeolite) is generally anionic. Cations that balance the charge of the anionic framework are loosely associated with the framework. The non-framework cations can be exchanged with cations, or counter cations, desired for a particular application. In some embodiments, the zeolite may be associated with an exchanged metal (e.g., copper). In some embodiments, the zeolite may be associated with a counter cation. The counter cation may comprise a metal, or exchanged metal. For example, the counter cation may comprise copper. In some embodiments, the counter cation may comprise a combination of sodium and copper. In some embodiments, the counter cation may comprise a combination of copper and hydrogen. In some embodiments, the counter cation may comprise a combination of copper and zinc. In some embodiments, the counter cation may comprise iron. In some embodiments, the counter cation may comprise cobalt.

According to some embodiments, in which the counter cation comprises copper and the framework comprises aluminum, the ratio of copper atoms to aluminum atoms within the catalyst, as calculated using inductively coupled plasma mass spectrometry (ICP-MS), may be at least 0.1, 0.2, 0.3, 0.4, 0.5, 0.6, 0.7, 0.8, or 0.9. The ratio of copper atoms to aluminum atoms may be less than or equal to 1.0, 0.9, 0.8, 0.7, 0.6, 0.5, 0.4, 0.3, or 0.2. Combinations of these ranges are also possible, for example, the ratio of copper atoms to aluminum atoms may be at least 0.5 and less than or equal to 0.8. Other values are also possible.

According to some embodiments, the catalyst may be selected for characteristics related to its pore structure, which may affect the performance of the process. For example, according to some embodiments, the catalyst may be microporous, used herein to refer to a catalyst having an average pore diameter of less than 2 nm. According to some embodiments, the catalyst may be mesoporous, used herein to refer to a catalyst having an average pore diameter of from 2 nm to 50 nm. According to some embodiments, the zeolite structure may contain cages.

According to one or more embodiments, the continuous, catalytic, low temperature, vapor phase oxidation of methane into methanol over an inorganic catalyst as disclosed herein may be utilized for the production of scalable designs for single step, small-scale GTL plants. Small modular GTL plants could be deployed at, for example, at stranded gas wells where conventional GTL plants would be too expensive to produce methanol at competitive prices.

According to certain embodiments, the methods generally disclosed herein may be practiced using relatively inexpensive materials to increase the economic efficiency of operation. For example, copper, a relatively inexpensive metal, may be utilized in commercially available catalysts. Meanwhile, cheap and green reactants such as oxygen and water may be used as components in the atmosphere surrounding the catalyst during alcohol production. Furthermore, the continuous, vapor phase production of methanol from methane described herein can be easily scaled to industrial demands.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Thus, as used herein, the term "alkyl" includes straight, branched and cyclic alkyl groups.

The following examples are intended to illustrate certain embodiments of the present invention, but do not exemplify the full scope of the invention.

EXAMPLES

First Non-Limiting Example

The discovery of large shale gas reservoirs and advances in extraction techniques has motivated methane to be used as a transportation fuel. A common strategy to convert methane into higher valued fuels is the gas-to-liquids (GTL) process of steam reforming methane into syngas (CO and $H_2$) and subsequent reaction into methanol, but GTL requires large scales and billions in capital investment. To reduce unit operations, cost, and size of GTL plants, the direct, selective oxidation of methane into methanol has attracted significant interest. Copper exchanged zeolites ZSM-5 and mordenite (MOR) are of particular importance due to similarities in their active sites to methane monooxygenase enzymes. These zeolites oxidize methane at low temperatures (>423 K) using molecular oxygen. Yet, methane is strongly bound to the copper active site or Bronsted acid sites as surface methoxy species, requiring water to extract methanol while simultaneously deactivating the active sites. Here we report the first continuous, catalytic, low temperature, vapor phase oxidation of methane into methanol over Cu-ZSM-5 and Cu-MOR. Stable catalytic activity over Cu-ZSM-5 was observed over several days using a simple mixture of methane, oxygen, and water between 473 K and 498 K. Other zeolite topologies exhibit catalytic activity, and activity is enhanced with zeolite structures containing cages. Our results demonstrate the first true biomimetic activity of copper exchanged zeolites related to methane monooxygenase enzymes as well as the microenvironment stabilizing the active site. We anticipate our work to be the genesis of scalable designs for single step, small-scale GTL plants. Techno-economic simulations predict $1.7 billion USD value by deploying modular GTL plants to stranded gas wells and then shifting plants to other wells as a function of market demand and well capacity. Small GTL plants could produce methanol at competitive prices if deployed at stranded gas wells where conventional GTL plants would be too expensive.

Catalytic activity in Cu—Na-ZSM-5 (Cu/Al=0.37, Na/Al=0.26) and Cu—H-ZSM-5 (Cu/Al=0.31) was observed for several days at 483 K. Initially, Cu—Na-ZSM-5 was activated under $O_2$ for 5 hrs at 823 K, cooled to reaction temperature at 483 K, and then purged under He for 1 hr. After reaction with $CH_4$ for 30 min, water was introduced into the vapor phase via a saturator maintained at 298 K. A pulse of methanol evolved from the Cu—H-ZSM-5 surface, corresponding to 37 μmol $g_{cat}^{-1}$ of stoichiometric methanol extracted. The methanol rate then reached steady state at 0.0144 μmol $min^{-1}$ $g_{cat}^{-1}$. The only additional product generated was $CO_2$ at a rate of 0.0064 μmol min $g_{cat}^{-1}$. The steady-state conversion of the reaction was 0.0013% and methanol selectivity was 71.0%. Most remarkably, the steady-state methanol rate persisted without deactivation. Maintaining this rate for 4.5 days, a total of 88 μmol $g_{cat}^{-1}$ of methanol was extracted at steady state, or 2.4 times the stoichiometric amount. This amount was roughly five times the highest stoichiometric extraction from Cu—Na-ZSM-5 and twice as high from Cu-SSZ-13. This implied turnover of surface species on the surface of Cu—Na-ZSM-5. The same activity was observed to occur over Cu—H-ZSM-5. 82 μmol $g_{cat}^{-1}$ of stoichiometric methanol initially produced followed by a steady state rate of 0.030 μmol $min^{-1}$ $g_{cat}^{-1}$ of methanol. Over 12 days, 491 μmol $g_{cat}^{-1}$ of methanol was produced.

To verify if turnover occurred, Cu—Na—ZSM-5 was reacted with $^{13}CH_4$ to observe an isotopic shift in methanol coming off the zeolite surface. Cu—Na-ZSM-5 (Cu/Al=0.37, Na/Al=0.26) was pretreated under similar conditions described above but was reacted with 18% $^{13}CH_4$/He at 498 K for 30 min. Then $^{12}CH_4$ and water were used to extract methanol from the zeolite. The methanol and $CO_2$ produced initially were $^{13}C$ labelled, as evidenced by the high ratio of the mass fragments 33.1/31.1 and 45/44. However, as the reaction rate approached steady state, both ratios 33.1/31.1 and 45/44 approached 0.01, which was consistent with oxidation and extraction of only $^{12}CH_4$. After collecting 18.5 μmol $g_{cat}^{-1}$ at steady state, the space velocity was reduced. Then the gas flow was switched to $^{13}CH_4$ for 30 min. The 33.1/31.1 and 45/44 ratios spiked after the $^{13}CH_4$ pulse and eventually settled to their initial values. The appearance of $^{13}CH_3OH$ indicated the direct incorporation of gaseous $^{13}CH_4$ into the product, thus showing turnover on the catalyst surface. The same phenomenon was also observed over Cu—H-ZSM-5.

In an effort to understand the effect of oxygen on catalytic activity, the partial pressure oxygen was varied. As the concentration of $O_2$ decreased, the observed methanol rate remained constant, showing the rate was 0 order with respect to $O_2$. However, completely eliminating $O_2$ from the reactant stream quenched any catalytic activity. Using a CuO oxygen trap to reduce the $O_2$ content <0.1 ppm, Cu—Na—ZSM-5 was activated under He for 5 hrs at 823 K, cooled to 483 K, and then underwent catalytic methane oxidation. While the $O_2$ trap was in place, no methanol could be detected in the gas phase. After the reaction mixture bypassed the oxygen trap, the $O_2$ concentration increased to 25 ppm and catalytic activity evolved after a 300 min induction period. This showed that $O_2$ is adsorbed onto a small number of surface sites acting as the oxidizing agent for catalytic methane oxidation.

While $O_2$ did not appreciably change the catalytic methane oxidation rate above 25 ppm, the thermal pretreatments of Cu—Na-ZSM-5 did affect the observed catalytic rate. When Cu—Na-ZSM-5 was heated and soaked under $O_2$ for 5 hrs at 823 K, the steady state rate was 0.0144 μmol $min^{-1}$ $g_{cat}^{-1}$ methanol. The same rate was achieved when Cu—Na-ZSM-5 was heated to 823 K under $O_2$ and soaked under He at 823 K for 5 hrs. However, When Cu—Na-ZSM-5 was heated and soaked under He (20 ppm $O_2$) at 823 K for 5 hrs, the steady-state rate was 0.010 μmol $min^{-1}$ $g_{cat}^{-1}$ methanol. This implied the deactivation of an active site with a rate of about 0.005 $min^{-1}$ $g_{cat}^{-1}$ methanol at 483 K and at least two active sites exist for the catalytic oxidation of methane into methanol.

The development of steady-state, catalytic methane oxidation activity was not only affected by thermal treatments but also by the presence of water in the reaction stream. Water broke through the Cu—Na-ZSM-5 bed after 25 min, causing a large pulse of methanol to evolve from the stoichiometric Cu—O—Cu active sites persisting for 600 min before reaching the catalytic methanol production. When Cu—Na-ZSM-5 was heated under $O_2$ to 823 K and then soaked 5 hrs under He, only a trace of the Cu—O—Cu sites remained intact. However, catalytic methanol production only appeared after an induction period of 240 min. The same induction period was observed when Cu—Na-ZSM-5 was exposed to saturated water vapor for 240 min before reaction with methane. As expected, no stoichiometric methanol was extracted after the hydrolysis of the Cu—O—Cu sites, but methanol activity became observable after 100 min and reached the same catalytic rate after 240 min. These experiments showed water played a role in the formation of the catalytic active sites in Cu—Na-ZSM-5.

In addition to the formation of the catalytic active sites in Cu—Na-ZSM-5, water competitively adsorbed to the active site to prevent methane oxidation activity. The rate of methanol production exhibited a first order dependence on methane partial pressure. The catalytic rate also increased linearly as the reaction pressure was increased from 0.1 to 1.6 MPa. As the reaction pressure increased, the partial pressure of water decreased relative to that of methane and oxygen. Coupled with oxygen being zero order with respect to the methanol rate, water had an antagonistic effect on the catalytic methane oxidation rate. This was likely caused by the weak adsorption of methane on $Cu^{2+}$ ions relative to water molecules.

Catalytic methane oxidation activity was observed to occur in several other zeolite topologies. The industrial zeolites beta (BEA), mordenite (MOR), ferrierite (FER), faujasite (Y), and chabazite (CHA) were all exchanged with copper and tested. For Cu/Al~0.30, catalytic activity was highest for ZSM-5 compared to BEA, FER, and MOR, suggesting there may be optimal channel size to form the catalytic active site. For zeolites with cage structures, SSZ-13 had the highest activity along with SAPO-34 (both CHA) compared to Y and amorphous MCM-41. This also suggested an intermediate cage size in the zeolite framework may stabilize the active site.

From the kinetic studies conducted and the effect of zeolite topology, we could postulate a reaction mechanism for catalytic methane oxidation. Under reaction conditions, the zeolite is exposed to water at elevated temperature (473-498 K), causing Cu speciation to change. In Cu-SSZ-13, dehydrated $Cu^{2+}$ migrates from the 6-membered ring to the cages. Migration reduces the strength of interaction between Cu and the zeolite framework as well as making reduction of $Cu^{2+}$ facile. Similar migration occurs within zeolites without cages, such as Cu-MOR. Under SCR reaction conditions in Cu-SSZ-13, hydrated Cu ions migrate to form transient, active Cu dimers below 523 K. The similarities in reaction conditions between methane oxidation and SCR reactions could suggest the formation of highly mobile and transient, hydrated Cu monomers or dimers. These transient species would have water surrounding Cu in its first coordination shell, requiring temporary desorption of water molecules to allow the interaction of oxygen or methane. The interaction of oxygen would activate some copper-oxo species active for methane oxidation. This species could then react with methane to form strongly bound methanol requiring water for extraction. However, the active copper-oxo species could also react with water to restore the hydrated Cu precursor, consistent with the inhibitory effect of water relative to methane as well as the need for high methane partial pressures. Lastly, the migration and formation of these transient copper species could explain the induction period observed before the onset of catalytic methane oxidation.

Most remarkably, methane was catalytically oxidized into methanol without the addition of any oxidizing agent after the initial activation step. Thermodynamics dictates the following equilibrium constants at 483 K for $O_2$ or water as oxidizing agents of methane:

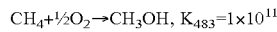

$CH_4 + \frac{1}{2}O_2 \rightarrow CH_3OH$, $K_{483} = 1 \times 10^{11}$

$CH_4 + H_2O \rightarrow CH_3OH + H_2$, $K_{483} = 1.4 \times 10^{-13}$

Under reaction conditions for methane oxidation, the thermodynamic reaction rate of water splitting was four orders of magnitude lower than the experimentally observed rate of 0.0144 μmol $min^{-1}$ $g_{cat}^{-1}$. On the other hand, the thermodynamic rate of 25 ppm of oxygen as the oxidizing agent was 0.08 μmol $min^{-1}$ $g_{cat}^{-1}$ methanol. These calculated rates agree with experimental evidence showing oxygen, or other oxidizing agent, is necessary for methane oxidation to occur. A CuO oxygen trap installed before the reactor reduced the $O_2$ content in the reaction stream to <0.1 ppm. At <0.1 ppm $O_2$, Cu—Na—ZSM-5 was activated under He for 5 hrs at 823 K, cooled to 483 K, and then underwent catalytic methane oxidation as described above. While the $O_2$ trap was in place, no methanol could be detected in the gas phase. After the reaction mixture bypassed the oxygen trap, the $O_2$ concentration increased to 25 ppm and catalytic activity evolved after a 300 min induction period. The converse experiment showed catalytic activity could be shut off if the $O_2$ was eliminated from the reaction mixture. When Cu—Na-ZSM-5 was calcined under $O_2$ at 823 K for 5 hrs, the steady state rate of 0.0139 μmol $min^{-1}$ $g_{cat}^{-1}$ methanol at 483 K was observed. When the reactant mixture was directed through the $O_2$ trap, the activity quickly dropped to 0.0058 μmol $min^{-1}$ $g_{cat}^{-1}$ methanol and eventually stopped.

Because multiple steady states were achieved during the deactivation of Cu—Na-ZSM-5 under <0.1 ppm $O_2$, multiple catalytic methane oxidation sites are likely to exist. Various thermal pretreatments of Cu—Na-ZSM-5 were found to change the steady-state methane oxidation rate. When Cu—Na-ZSM-5 was heated and soaked under $O_2$ for 5 hrs at 823 K, the steady state rate was 0.0144 μmol $min^{-1}$ $g_{cat}^{-1}$ methanol. The same rate was achieved when Cu—Na-ZSM-5 was heated to 823 K under $O_2$ and soaked under He at 823 K for 5 hrs. However, When Cu—Na-ZSM-5 was heated and soaked under He (20 ppm $O_2$) at 823 K for 5 hrs, the steady-state rate was 0.010 μmol $min^{-1}$ $g_{cat}^{-1}$ methanol. This implied the deactivation of an active site with a rate of about 0.005 $min^{-1}$ $g_{cat}^{-1}$ methanol at 483 K. The difference in activity between these experiments was also roughly equal to the intermediate steady-state achieved during the deactivation of Cu—Na-ZSM-5 under the $O_2$ trap (0.0058 $min^{-1}$ $g_{cat}^{-1}$ methanol). Both experiments shows that at least two active sites exist for the catalytic oxidation of methane into methanol.

The order of reactants methane and water added to Cu—Na-ZSM-5 affected the onset of catalytic activity. Conventionally, stoichiometric methane oxidation and extraction of methanol from copper-exchanged zeolites has been conducted by activating the zeolite at high temperature under O2, cooling the zeolite either using liquid water or vapor phase water diluted in He.

Second Non-Limiting Example

Using copper exchanged zeolites of various frameworks, we found gaseous methanol can be produced isothermally from 190° C.-230° C. in the presence of methane, oxygen, and water. Copper exchanged zeolites were prepared by aqueous ion exchange of 1 gram of commercial ZSM-5, MOR, ferrierite, and beta (Zeolyst International, Si/Al=11.5, 10, 10 and 12.5 respectively) in 60 mL of 0.01M copper acetate dihydrate or copper nitrate trihydrate at 25° C. These zeolites could be in the sodium or Bronsted acid forms before ion exchange, producing Cu—H- or Cu—Na-zeolites (e.g. Cu—Na-ZSM-5 or Cu—H-ZSM-5). The mixture was stirred for 12 hours and then vacuum filtered. The precipitate was thoroughly washed with $dH_2O$ and dried overnight at 110° C. Elemental composition was determined using inductively coupled plasma mass spectrometry and measured between 0.8-2.5 wt % copper.

2.0 grams of the prepared copper exchanged zeolite was placed into a packed-bed flow reactor. The zeolite was treated under flowing oxygen at 550° C. for 2-5 hours, and then cooled to reaction temperature (190° C.-230° C.). Cu-ZSM-5 was flushed with helium to purge trace oxygen. The gas flow was then switched to methane to deposit surface bound methoxy or methanol groups. Methanol was extracted from the zeolite by redirecting methane flow through a water saturator kept at 25° C.

Methane Oxidation Over Cu-ZSM-5

After Cu-ZSM-5, in the sodium or Bronsted acid forms, is activated under oxygen at 550° C., an initial pulse of methanol was generated from the zeolite and eventually settled to a steady-state methanol production rate. For Cu—H-ZSM-5 (Cu/Al=0.31), 1.81 µmol h$^{-1}$ g$_{cat}$$^{-1}$ of methanol was generated, while 0.88 µmol h$^{-1}$ g$_{cat}$$^{-1}$ methanol came from Cu—Na-ZSM-5 (Cu/Al=0.37). The catalysts were remarkably stable, with Cu—H-ZSM-5 operating for 12 days on stream with no deactivation, as shown in FIG. 1. The data shown in FIG. 1 represent: Low temperature methane oxidation over (■) Cu—Na-ZSM-5 (Cu/Al=0.37, Na/Al=0.27) and (▲) Cu—H-ZSM-5 (Cu/Al=0.31). The data shown in FIG. 1 were produced according to the following conditions: Catalyst Pretreatment: 5 h under oxygen at 550° C.; Reaction Conditions: T=210° C., WHSV=2400 mL hr$^{-1}$ g$_{cat}$$^{-1}$, P$_{CH4}$=98.13 kPa, P$_{H2O}$=3.2 kPa, P$_{O2}$=25 ppm. Methane oxidation over (□) Cu—Na-ZSM-5 (Cu/Al=0.37, Na/Al=0.27) without methane in the gas stream. Catalyst Pretreatment: 5 h under oxygen at 550° C.; Reaction Conditions: T=210° C., WHSV=2400 mL hr$^{-1}$ g$_{cat}$$^{-1}$, P$_{He}$=98.13 kPa, P$_{H2O}$=3.2 kPa, P$_{O2}$=25 ppm.

Figure 2:
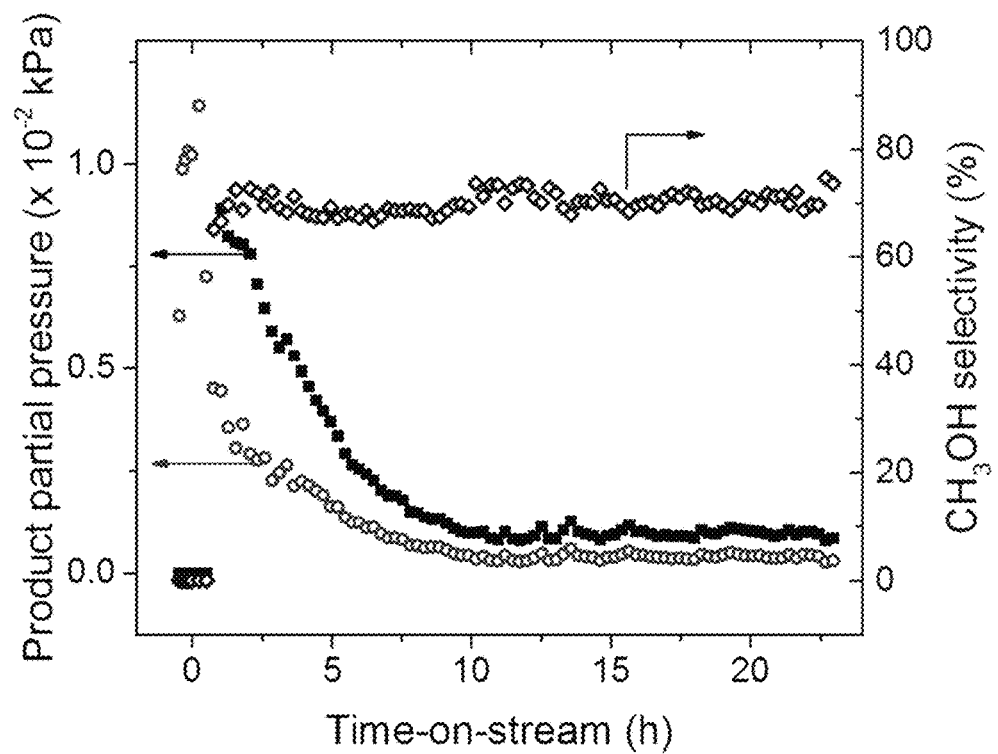
FIG. 2 is a graphical representation of methanol and carbon dioxide production and selectivity, according to one or more non-limiting embodiments.

Only methanol and carbon dioxide are produced from methane oxidation. Over Cu—Na-ZSM-5 (Cu/Al=0.37, Na/Al=0.27), carbon dioxide was initially produced in large quantities, but decays over time. The steady-state conversion of methane was 0.0013% with 71% selectivity towards methanol (FIG. 2). This shows that Cu—Na-ZSM-5 is a selective catalyst for the formation of methanol from methane. The results shown in FIG. 2 were produced under the following conditions: Catalyst pretreatment: 5 h at 550° C. under flowing oxygen, cooled to 210° C. under oxygen flow and then purged under He for 0.5 h. Initial methane oxidation: 0.5 h under 2400 mL h$^{-1}$ g$_{cat}$$^{-1}$ of methane at 210° C. Reaction conditions: T=210° C., WHSV=2400 mL h$^{-1}$ g$_{cat}$$^{-1}$, P$_{CH4}$=98.1 kPa, P$_{H2O}$=3.2 kPa, P$_{O2}$=0.0025 kPa (25 ppm). The following symbols are represented in FIG. 2: (■) CH$_3$OH partial pressure (kPa); (○) CO$_2$ partial pressure (kPa); and (◇) CH$_3$OH selectivity.

The apparent activation energy of Cu—Na-ZSM-5 was calculated to be 54±4.8 kJ/mol, where 4.8 denoted the bounds of the 95% confidence interval.

Proof of Necessary Reactants in Methane Oxidation

Stoichiometric oxidation of methane over copper exchanged zeolites requires oxygen to activate the oxidation active site, methane as the carbon source, and water to extract the surface bound methoxy group. We have proved the same common reagents are needed to perform catalytic methane oxidation into methanol over Cu-ZSM-5.

To study the role of oxygen in the methane oxidation reaction, the oxygen partial pressure was reduced from several percent to parts-per-million (ppm) concentration in the gas stream. The methanol generation rate remained constant around 0.60 µmol h$^{-1}$ g$_{cat}$$^{-1}$ until oxygen was completely removed from the gas stream. Oxygen was reduced to <0.1 ppm using an oxygen trap activated under 2% hydrogen gas at 190° C. With this oxygen trap in place, Cu—Na—ZSM-5 was heated under helium at 550° C. for 5 hours and cooled to reaction temperature for the same reaction procedure outlined above. No methanol was generated from Cu—Na-ZSM-5 while the reactant gases were directed through the oxygen trap. However, methanol production was restored when the reactant gas stream bypassed the oxygen trap, indicating oxygen is necessary for methane oxidation over copper exchanged zeolites.

The methane was confirmed to be the carbon source for methanol using $^{13}$C-isotopically labeled experiments. Over both Cu—Na-ZSM-5, 17% $^{13}$CH$_4$ in helium was used to deposit surface bound $^{13}$C-methoxy species after pretreatment under oxygen at 550° C. However, the carbon source was switched to $^{12}$CH$_4$ during extraction, ensuring $^{13}$C-methanol would be produced in the initial pulse of methanol but $^{12}$C-methanol must be produced at steady state. Tracking mass 33.1 (32 was not tracked due to residual oxygen and nitrogen impurities in the mass spectrometer) for $^{13}$C-methanol showed initial production of $^{13}$C-methanol that went to zero as methanol production transitioned from the stoichiometric to catalytic regimes. A control reaction using only $^{12}$CH$_4$ for both the deposition of methoxy species and extraction had zero mass 33.1 in both stoichiometric and catalytic regimes. After Cu—Na-ZSM-5 reached steady state from its initial coverage of $^{13}$C-methanol, steady-state production of $^{12}$C-methanol was maintained for a total of 21 h, corresponding to 18.5 µmol g$_{cat}$$^{-1}$ of catalytic methanol collected. The weight hour space velocity was then reduced to 300 mL h$^{-1}$ g$_{cat}$$^{-1}$. After stabilizing steady-state methanol activity, Cu—Na—ZSM-5 was exposed to $^{13}$CH$_4$ and water for 0.5 h after which $^{12}$CH$_4$ was reintroduced into the gas stream. A large $^{13}$C-carbon dioxide and methanol pulse was observed to form and then reverted back to the $^{12}$C products, thereby verifying catalytic turnover over the Cu-ZSM-5 surface and methane incorporation into methanol.

Similar results were observed for isotopically labeled experiments over Cu—H-ZSM-5 (Cu/Al=0.31). Activating Cu—H-ZSM-5 in flowing oxygen at 550° C. and after initial reaction with 17% $^{13}$CH$_4$ in helium at 210° C., a pulse of $^{13}$C-methanol (mass 33) was extracted from the its surface. This pulse of $^{13}$C-methanol decayed to zero (all $^{12}$C-methanol) as methanol production transitioned into the catalytic regime. Using $^{12}$CH$_4$ for the initial deposition of methoxy species on the Cu—H-ZSM-5 surface resulted in virtually no $^{13}$C-methanol production, confirming catalytic turnover over Cu—H-ZSM-5.

A protic solvent such as water was necessary to extract methanol from the catalyst surface. Without water in the reaction stream, no methanol was observed in the product stream. The methanol production rate gradually increased as the water partial pressure increased.

Methane Oxidation Over Other Zeolite Topologies

Catalytic, vapor phase, low temperature methane oxidation into methanol also occurred on other zeolite frameworks, such as Cu-MOR. The apparent activation energy of Cu—H-MOR (Cu/Al=0.14) was 149±2 kJ/mol, while that of Cu—Na-MOR (Cu/Al=0.14) was 92±3 kJ/mol. Their catalytic rates at 210° C. were 0.84 µmol h$^{-1}$ g$_{cat}$$^{-1}$ and 0.30 µmol h$^{-1}$ g$_{cat}$$^{-1}$. Thus, Cu-MOR also exhibits catalytic activity for methane oxidation into methanol.

Other zeolites exhibiting catalytic activity are listed below. All of the industrial zeolites MOR, FER, BEA, (Table 1) and Y exhibit catalytic activity (Table 2). Even MCM-41, an amorphous silicate, has some activity. Comparing copper content across zeolites, BEA (Cu/Al=0.33) and FER(Cu/Al=0.12) appear less active than ZSM-5 of similar Cu content. Zeolites with caged structures, mainly CHA (Table 2), are promising due to their high activity (3.12 µmol h$^{-1}$ g$_{cat}^{-1}$ vs. 0.88 µmol h$^{-1}$ g$_{cat}^{-1}$ for Cu-ZSM-5) and site-time yield per Cu atom (6.1 vs. 2.2 mmol h$^{-1}$ mol Cu$^{-1}$). Structures AEI and AFX, with similarly sized cages to CHA, also have higher activity and site-time yield than that of ZSM-5 (4.14 and 2.40 µmol h$^{-1}$ g$_{cat}^{-1}$ and 9.3 and 4.1 mmol h$^{-1}$ mol Cu$^{-1}$). Lastly, silicoaluminophosphates like SAPO-34 (CHA topology), are active for catalytic methane oxidation. At low copper content, its methanol production rate was low (0.84 µmol h$^{-1}$ g$_{cat}^{-1}$), but its site-time yield was extremely high (9.3 mmol h$^{-1}$ mol Cu$^{-1}$).

TABLE 1

Zeolite topologies exhibiting catalytic methane oxidation activity. These zeolites do not have cage structures

| Framework | Structure | Channel Size | Si/Al | Cu/Al | Methanol (µmol/h/g$_{cat}$) | Site-Time Yield (mmol/h/mol Cu) |
|---|---|---|---|---|---|---|
| MFI | H-ZSM-5 | 5.3 × 5.6, 5.1 × 5.5 | 13.9 | 0.13 | 0.84 | 6.0 |
| FER | H-Ferrierite | 4.2 × 5.4, 3.5 × 4.8 | 10.6 | 0.12 | 0.44 | 2.7 |
| MOR | H-Mordenite | 6.5 × 7, 2.6 × 5.7 | 11.1 | 0.14 | 0.84 | 4.6 |
| MFI | H-ZSM-5 | 5.3 × 5.6, 5.1 × 5.5 | 13.2 | 0.31 | 1.79 | 5.2 |
| BEA | H-Beta | 6.6 × 6.7, 5.6 × 5.6 | 13.3 | 0.33 | 0.80 | 2.4 |
| MOR | H-Mordenite | 6.5 × 7, 2.6 × 5.7 | 10 | 0.77 | 0.9 | 1.1 |
| MCM-41 | MCM-41 | 30 | 16.1 | 0.74 | 0.36 | 0.6 |

TABLE 2

Zeolite topologies exhibiting catalytic methane oxidation activity. These zeolites have cage structures (minus ZSM-5)

| Framework | Structure | Cage Shape | Cage Size | Channel Size | Si/Al | Cu/Al | Methanol (µmol/h/g$_{cat}$) | Site-Time Yield (mmol/h/mol Cu) |
|---|---|---|---|---|---|---|---|---|
| MFI | Na—ZSM-5 | | | 5.3 × 5.6, 5.1 × 5.5 | 13.6 | 0.37 | 0.88 | 2.2 |
| CHA | Na—SSZ-13 | Ellipsoidal | 9.4 × 9.4 × 12.7 | 3.8 × 3.8 | 13.8 | 0.50 | 3.12 | 6.1 |
| CHA | SAPO-34 | Ellipsoidal | 9.4 × 9.4 × 12.7 | 3.8 × 3.8 | 0.6 | 0.02 | 0.84 | 7.9 |
| AEI | Na—AEI | Ellipsoidal | 9.7 × 11.9 × 12.6 | 3.8 × 3.8 | 15 | 0.30 | 4.14 | 9.3 |
| AFX | Na—AFX | Ellipsoidal | 8.7 × 10.1 × 15.8 | 3.4 × 3.6 | 15 | 0.28 | 2.40 | 4.1 |
| FAU | Na—Y | Spherical | 9.6 × 9.6 | 7.4 × 7.4 | 4.6 | 0.45 | 0.30 | 0.3 |

Catalytic Methane Oxidation as a Function of Thermal Pretreatment and the Addition of Reactants Catalytic methane oxidation into methanol can be achieved over copper exchanged zeolites over a wide range of thermal pretreatments at elevated temperature as well as the order of addition of reactant gases (methane, oxygen, water). Despite calcining Cu—Na-ZSM-5 under pure oxygen (black trace), heating under oxygen and calcining under He (20 ppm oxygen, red trace), or heating and calcining under helium (20 ppm oxygen, purple trace), catalytic methanol production was achieved at 0.88 or 0.60 µmol h$^{-1}$ g$_{cat}^{-1}$. This study shows that any partial pressure of oxygen can be used during calcination at elevated temperatures (>400° C.).

After calcination, the reactants methane, oxygen, and water can be added to the reaction mixture in any order. Conventionally, stoichiometric methanol production is achieved by flowing methane over Cu-ZSM-5 after calcination. It has been demonstrated herein that catalytic methanol production is observed after the initial pulse of stoichiometric methanol. Catalytic methanol production develops over Cu—Na-ZSM-5 when first flowing 3.2 kPa water, 25 ppm oxygen, balance helium after calcination and then adding methane to the gas stream. Lastly, flowing methane and water after calcination in helium (<0.1 ppm oxygen) and then adding trace amounts of oxygen results in catalytic methanol production as well. All of these examples over Cu—Na-ZSM-5 indicate catalytic methanol production can be achieved over copper exchanged zeolites irrespective of the sequence of gaseous reactants introduced.

Catalytic Methane Oxidation at Elevated Pressure

Figure 3:
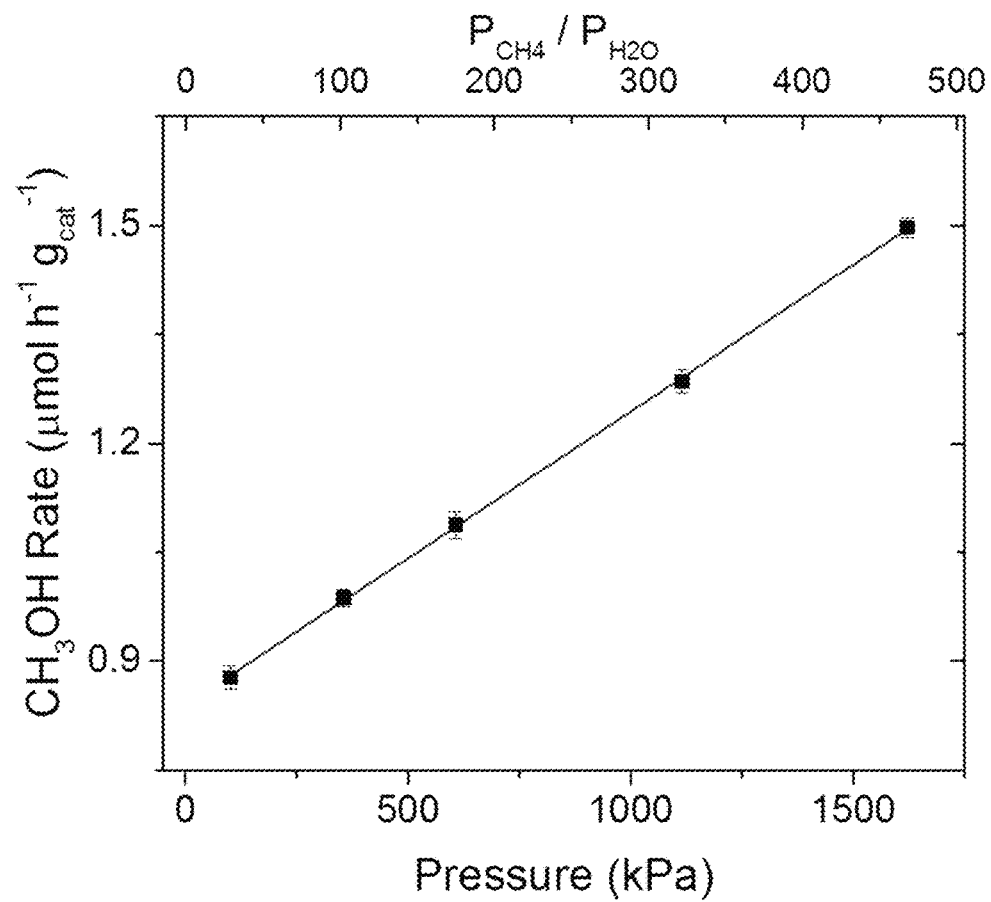
FIG. 3 is a graphical representation of a relationship between pressure and a steady state production rate of methanol, according to one or more non-limiting embodiments.

Methanol production rates can be increased by running the methane oxidation reaction at pressures higher than atmospheric. Methanol production rates increased from 0.88 to 1.5 µmol h$^{-1}$ g$_{cat}^{-1}$ as the total pressure of the reactor was increased from atmospheric pressure to 1600 kPa (FIG. 3) operating at 210° C., WHSV of 2400 mL h$^{-1}$ g$_{cat}^{-1}$, and 3.2 kPa water and balance methane and oxygen at a methane-to-oxygen partial pressure ratio of 7255. Operating methane oxidation reactions at even higher total pressure may further increase methanol production rates.

Direct Synthesis of Copper Containing Zeolites and Silicoaluminophosphates and its Reactivity in Catalytic Methane Oxidation into Methanol We have demonstrated that copper can be directly introduced into the zeolite during synthesis, as opposed to post synthetic ion exchange described above, and exhibit catalytic activity for low temperature methane oxidation. Copper is introduced directly into aluminosilicate and silicoaluminophosphate materials through the addition of copper sulfate and the chelating agent tetraethylenepentamine (TEPA) during hydrothermal synthesis. The most well-known examples are the direct synthesis of Cu-SSZ-13 and Cu-SAPO-34 (both of the chabazite structure) for use in the selective catalytic reduction of nitrogen oxides.

Figure 4:
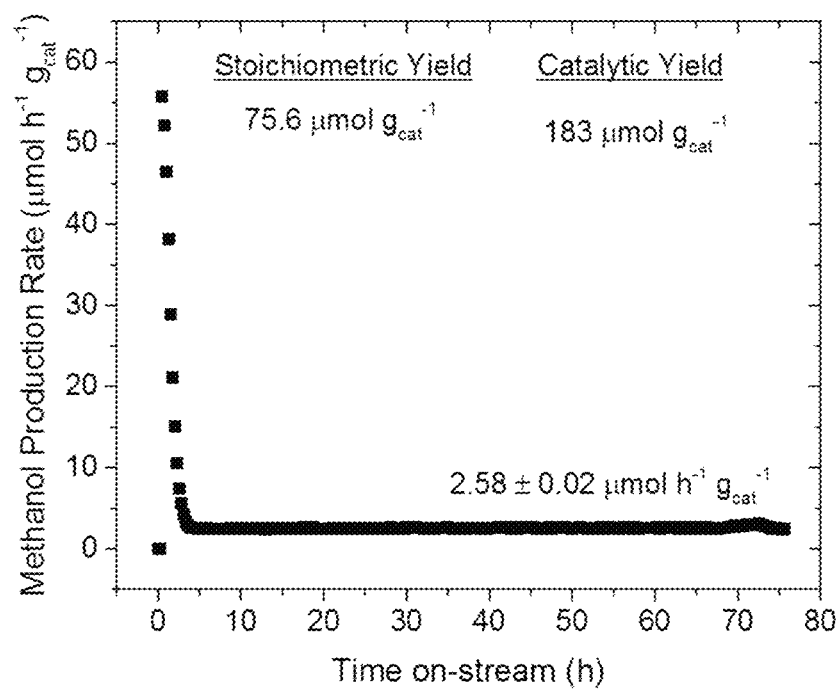
FIG. 4 is a graphical representation of methanol production, according to one or more non-limiting embodiments.

The direct synthesis of Cu-SAPO-34-D was prepared following the procedure by Martinez-Franco and coworkers. Cu-SAPO-34-D was then tested for catalytic methane oxidation following the same experimental setup and reaction conditions described above. Cu-SAPO-34-D exhibited the same pulse of stoichiometric methanol during extraction. Methanol production settled to a steady-state rate of 2.58 µmol h$^{-1}$ g$_{cat}^{-1}$ in the catalytic regime (FIG. 4). This shows copper containing zeolites and silicoaluminophosphates can be directly synthesized and exhibit catalytic activity for low temperature methane oxidation into methanol. The data in FIG. 4 were the result of the following conditions: Methane oxidation over Cu-SAPO-34-D (directly synthesized with TEPA, Si/Al=0.38, Cu/Al=0.15). Catalyst Pretreatment: 5 h under oxygen at 550° C.; Reaction Conditions: WHSV=2400 mL hr$^{-1}$ $g_{cat}^{-1}$, $P_{CH4}$=98.13 kPa, $P_{H2O}$=3.2 kPa, $P_{O2}$=25 ppm.

The direct synthesis of Cu-SSZ-13 using TEPA as a chelating agent resulted in an aluminosilicate material that was highly active for catalytic methane oxidation. Cu-SSZ-13-D samples with Si/Al=14-16 and Cu/Al from 0.027 to 0.30 were pretreated under 1% oxygen in helium at 550° C., cooled to 220° C., and then exposed to a gas mixture of 6000 mL h$^{-1}$ $g_{cat}^{-1}$ of 88.3 kPa methane, 3.2 kPa water, 0.098 kPa oxygen, and helium balance. Steady-state methanol production rates were then collected for temperatures between 220-350° C. Catalytic methanol production rates were observed from 2 to 173 µmol h$^{-1}$ $g_{cat}^{-1}$ between 220-350° C. At reaction temperatures below 280° C., the methanol production rate generally increases with Cu content in the zeolite. However, low Cu content zeolites are less prone to oxidizing methanol into carbon dioxide. Thus the highest methanol production rates can actually be achieved with low Cu content Cu-SSZ-13-D zeolites at higher reaction temperature. Data shows the site-time yield achieved over Cu-SSZ-13-D was between 0.02 and 2.6 mol methanol (mol Cu)$^{-1}$ h$^{-1}$ at 350° C. for Cu/Al=0.04. The total conversion of methane, calculated from the sum of methanol, carbon dioxide, dimethyl ether, and ethane produced, reached as high as 0.1% over Cu-SSZ-13-D with Cu/Al=0.08.

Methanol production rates over Cu-SSZ-13-D are extremely stable. Operating at 350° C. under 6000 mL h$^{-1}$ $g_{cat}^{-1}$ of 88.3 kPa methane, 3.2 kPa water, 0.098 kPa oxygen, and helium balance, 63 µmol methanol h$^{-1}$ $g_{cat}^{-1}$ and 2.5 mol methanol (mol Cu)$^{-1}$ h$^{-1}$ was produced for 130 h on-stream without any noticeable deactivation. The cumulative methanol produced in this time interval was 342 mol methanol (mol Cu)$^{-1}$. Methanol selectivity was as high as 93% with the other side products as dimethyl ether and ethane. No appreciable amount of carbon dioxide was observed. Therefore, the one-pot synthesis of copper-exchanged aluminosilicate and silicoaluminophosphate materials with TEPA is a promising strategy to make highly active, stable, and selective catalysts for methane oxidation.

Bimetallic Copper-Metal Exchanged Zeolites for Catalytic Methane Oxidation

Other metals cations, in combination with copper, can be exchanged into zeolites to produce catalytic methane oxidation activity. Bimetallic exchanged zeolites are prepared in a similar manner to copper exchanged zeolites. During ion exchange, both copper acetate and another metal salt (acetate or nitrate) are added, in various ratios, to 1 gram of zeolite in 60 mL of water. The same stirring time, filtration process, and calcination procedure is followed for copper exchanged zeolites.

A Cu—Zn-SSZ-13 zeolite (CHA topology) has been shown to possess methane oxidation activity. The Cu—Zn-SSZ-13 zeolite was prepared from a 1:9 Cu:Zn ratio during ion exchange, resulting in Cu/Al=0.08 and Zn/Al=0.21. After calcination in 1% oxygen/helium at 550° C. and exposure to 3.2% water, 1% oxygen at 220° C. for 4 h, catalytic methanol production was observed at a rate of 3.0 µmol h$^{-1}$ $g_{cat}^{-1}$. Other combinations of metal cations, along with copper, are likely active for low temperature methane oxidation.

Methane Oxidation Over Copper Exchanged Zeolites with Various Framework Metals Atoms Zeolites can be synthesized with a variety of heteroatoms incorporated into its predominantly silicon dioxide framework. Elements isoelectronic with aluminum (+3), such as boron and gallium, have been incorporated into the framework of zeolites. Additionally, elements isoelectronic with silicon (+4), such as germanium, can also be substituted into the zeolite framework. A zeolite with any combination of aluminum, boron, or gallium with silicon or germanium can be exchanged with copper and show low temperature, catalytic methane oxidation activity.

Catalytic Methane Oxidation with Other Oxidizing Agents

Methane oxidation over copper-exchanged zeolites has been demonstrated using molecular oxygen ($O_2$) as the oxidizing agent, but other oxidizing agents can be utilized to achieve methanol production. Steady-state methanol production was achieved using nitric oxide (NO) as the oxidizing agent over copper exchanged Cu-SSZ-13 (Si/Al=9.6, Cu/Al=0.05). After activation under 1% oxygen in helium at 550° C. and cooling to 300° C., a steady-state methanol production rate of 1.36 µmol h$^{-1}$ $g_{cat}^{-1}$ was achieved with a reaction mixture of 0.25 kPa NO, 3.2 kPa water, 92.9 kPa methane, and helium balance at 5760 mL h$^{-1}$ $g_{cat}^{-1}$. Other oxidizing agents, such as nitrous oxide and ozone, are likely active for catalytic methane oxidation activity as well.

Advantages and Improvements Over Existing Methods and Materials

With petroleum becoming scarce and expensive, hydrocarbon sources for the fuel and chemical industries must shift to cheaper feedstocks. Methane, comprising the majority of natural gas deposits, is an attractive alternative because it is nontoxic, lower emission, and versatile as a C1 unit for Fischer-Tropsch synthesis. Advances in hydraulic fracturing techniques has exponentially increase methane extraction from wells, resulting in low and stable methane prices. Unfortunately, directly forming longer chain fuels from methane is endothermic due to its high bond enthalpy. Methane oxidation is exothermic, but its partially oxidized products, such as methanol, have weaker bond enthalpies and would be fully oxidized into carbon dioxide at the conditions needed for the initial oxidation.

Industrial Steam Reforming and Methanol Synthesis

The current industrial pathway to convert methane into methanol involves two capital-intensive reactions: steam reforming and methanol synthesis. Steam reforming converts methane and water into hydrogen and carbon monoxide gases. This "syngas" is then fed into a methanol synthesis unit where the syngas is converted into methanol or other hydrocarbons. Several drawbacks exist for this industrial pathway. Firstly, the technical complexity is high. Two reaction units must be built as well as associated separations units afterwards. Numerous cryogenic separations and other utilities are needed to purify the syngas effluent from steam reforming to allow methanol synthesis to proceed efficiently. Auxiliary operations within the gas-to-liquids plants accounts for roughly half of the plant cost. Such technical complexity requires extremely large scale production facilities, thereby incurring high capital costs for gas-to-liquids plants. Secondly, steam reforming is energy intensive due to the high temperatures required (>800° C.). Lastly, methanol synthesis requires high pressures (50-100 bar), incurring additional cost for compression pumps.

Biological Conversion of Methane into Methanol

To avoid the large scale production facilities needed to make steam reforming and methanol synthesis profitable, numerous alternatives have been researched for the direct partial oxidation of methane. The gold standard for the oxidation of methane into methanol is the methane monooxygenase enzymes, which can function in aqueous environments at ambient temperature and pH. However, the inherent problem with using enzymes industrially is their sensitivity to harsh temperatures and pH, difficulty of purifying large amounts of homogeneous enzyme, and difficulty in purification of alcohol products and enzyme from liquid water (solvent).

Inorganic catalysts for methane oxidation have been developed, but all suffer from at least one of the following deficiencies: expensive catalyst, low selectivity, high temperatures, or environmentally harmful reagents needed.

Oxidative Coupling to Higher Alkanes

Oxidative coupling of methane involves its partial oxidation into longer chain alkanes and water using alkaline earth oxides catalysts (Li doped MgO). However, high temperatures (>700° C.) are required to directly oxidize C—H bonds. Alkyl radicals are then produced, and at those temperatures undergo numerous side reactions into polymers, aromatics, or carbon dioxide, thus having very low selectivity and yield of short-chain alkanes (50% and 14% respectively for Li—MgO). Metal oxide catalysts at those temperatures are unstable. This makes oxidative coupling uneconomical even after decades of research.

Halogenation of Alkanes

Halogenation is the reaction of halogens with methane to form alkyl-halide intermediates and then dehydration and oxidation into alcohols. This is a heterogeneous process on catalysts such as $Br_2MoO_2$ on Zn-MCM-48. Overoxidation reduces alcohol selectivity to 50%, and catalytic activity is low with only 14% conversion. Loss of halogens during reaction results in strong acids HX (X=Cl, Br), both highly corrosive and environmentally harmful. Strong acids and residual halogens must be further separated from the product methanol.

Low Temperature Partial Oxidation of Alkanes

Low temperature partial oxidation of alkanes is of primary interest to avoid low selectivity and high energy inputs. The most efficient catalytic system is a homogeneous platinum catalyst dissolved in concentrated sulfuric acid. Methane conversion and selectivity into methanol has been reported to be 90% and 70% respectively. Despite such astonishing yields, this system is unusable at large scales due to its highly acidic conditions, expensive and unrecoverable catalyst, and separations cost between methanol and sulfuric acid. A heterogeneous analog to the Periana catalyst was developed, but still required strongly acidic conditions.

Iron exchanged ZSM-5 zeolites have utilized hydrogen peroxide to oxidize methane into methanol in the aqueous phase at low temperature (50° C.). Product extraction for Fe-ZSM-5 with copper promoters are quite high, achieving up to 7000 μmol gcat$^{-1}$ of methanol at 85% selectivity. However, the liquid phase reaction requires higher methane pressures (>30 bar) to ensure good mixing of gas and liquid phases. Lastly, the hydrogen peroxide oxidant is not efficiently used to oxidize methane. Elevated temperatures around 50° C. causes hydrogen peroxide to degrade into water. Along with spectator iron species within Fe-ZSM-5, hydrogen peroxide is consumed at 6 times the rate of methanol production. Based on the prices of $550/metric ton methanol and $500/metric ton hydrogen peroxide, this process cannot be economical at large scale.

Contrasted with the above methane oxidation pathways, methane oxidation over Cu-ZSM-5 and Cu-MOR overcomes all of the usual drawbacks of methane oxidation pathways. Copper is one of the cheapest metals ($5.30/kg) while ZSM-5 and mordenite are commercial catalysts. Cu—Na-ZSM-5 gives a selectivity to methanol around 75% at low reaction temperature (190-230° C.) while using cheap and green reactants such as oxygen and water. Lastly, the continuous, vapor phase production of methanol from methane over copper exchanged zeolites can be easily scaled to industrial demands.

Advantages of the Method and Materials Under Study

One of the most significant costs of natural gas processing is the transportation of the gas from its reserves to a chemical processing facility. 80% of natural gas is located in stranded sites, far away from chemical processing infrastructure. Two alternatives to the conversion of methane into liquid fuels is its compression or cryogenic freezing. However, the low energy density of compressed methane as well has high pressures requires numerous safety precautions to be taken. Liquid methane has a much higher energy density than compressed methane, but the high cost of cryogenic freezing as well as complex equipment needed to transport and reprocessing of the liquid into a usable form renders this options uneconomical over long transportation distances. However, we have demonstrated that methane can be directly converted into methanol, a liquid fuel easy to transport, in one reaction step over Cu-ZSM-5 and Cu-MOR. Indeed, process simulations show the conversion of methane into liquid fuels in the most economical choice for markets very far from large natural gas wells. With global energy demand sharply rising in the near future (citation), the distance to ship fuels will only increase.

The equipment required for the direct oxidation of methane into methanol is standard in any moderately sized production facility, and as such, could be quickly incorporated into an existing chemical plant. As such, the commercial capital needed to implement this methane oxidation reaction pathway will be minimal.

With the benefits above, we strongly believe that this technology will have a significant commercial impact on the chemicals and energy industry.

Third Non-Limiting Example

The direct catalytic conversion of methane to liquid oxygenated compounds, such as methanol or dimethyl ether, at low temperature using molecular oxygen is a grand challenge in C—H activation that has never been met with synthetic, heterogeneous catalysts. Herein is reported the first demonstration of direct, catalytic oxidation of methane into methanol with molecular oxygen over copper-exchanged zeolites at low reaction temperatures (483-498 K). Reaction kinetics studies show sustained catalytic activity and high selectivity for a variety of commercially available zeolite topologies under mild conditions (e.g., 483 K and atmospheric pressure). Transient and steady state measurements with isotopically labeled molecules confirm catalytic turnover. The catalytic rates and apparent activation energies are affected by the zeolite topology, with caged-based zeolites (e.g., Cu-SSZ-13) showing the highest rates. The discovery of catalytic sites in copper-exchanged zeolites will accelerate the development of strategies to directly oxidize methane into methanol under mild conditions.

To date, no man-made catalyst can convert methane ($CH_4$) and oxygen ($O_2$) directly into methanol ($CH_3OH$) at low temperature. For more than 100 years, the selective oxidation of this simple alkane has remained unsolved. This transformation, however, is essential to exploit our highly abundant natural gas reserves, particularly those located in distributed fields or stranded wells that cannot be accessed with large, capital-intensive reforming facilities. Although oxidative C—H bond activation of $CH_4$ is thermodynamically and kinetically accessible at low temperatures, the large bond dissociation energy (435 kJ mol$^{-1}$) of this molecule hinders C—H cleavage reactions via homolytic or heterolytic pathways. Consequently, few catalysts are capable of preventing over-oxidation to carbon dioxide ($CO_2$). Several alternative strategies for activating methane have been reported, including multi-step oxyfunctionalization with Periana catalysts, borylation, and electrophilic carbene insertion, but all have fallen short of producing methanol directly and do not use oxygen as the oxidizing agent. In contrast, methane monooxygenase enzymes are capable of oxidizing $CH_4$ selectively into $CH_3OH$ using $O_2$ at room temperature. Such biocatalyts are difficult to scale-up. Iron- and copper-exchanged zeolites are capable of selectively oxidizing $CH_4$ into surface-bound methoxy species by hosting active sites akin to those found in $CH_4$ monooxygenases. Despite their potential, these materials have only been shown to oxidize $CH_4$ to $CH_3OH$ stepwise and stoichiometrically with molecular oxygen ($O_2$) or catalytically with hydrogen peroxide, making the process prohibitively expensive. Here, we report the first instance of catalytic gas phase oxidation of $CH_4$ into $CH_3OH$ with $O_2$ under mild conditions. Copper-exchanged zeolite catalysts of various topologies maintain sustained activity and high $CH_3OH$ selectivity at 483 K while transient kinetic experiments with isotopically labeled molecules confirm catalytic turnover.

The stoichiometric oxidation of $CH_4$ to $CH_3OH$ over copper-exchanged zeolites is believed to occur over mono-(μ-oxo) dicupric cores or $[Cu_3O_3]^{2+}$ trimeric sites generated by flowing anhydrous $O_2$ over the zeolite at temperatures above 723 K. These highly reactive electrophilic metal-oxygen species are adept at attacking the strong C—H bonds of $CH_4$, generating surface-bound methoxy groups at temperatures below 473 K. Methoxy groups are typically extracted as $CH_3OH$ by reacting with $H_2O$, which deactivates the copper sites and necessitates high temperature reactivation under anhydrous $O_2$ to perform the next oxidation cycle. In the present study, stoichiometric and catalytic $CH_3OH$ production regimes are observed during the gas phase oxidation of $CH_4$ over copper-exchanged zeolites with the MFI topology in the sodium (Cu—Na-ZSM-5) or proton (Cu—H-ZSM-5) forms at 483 K and atmospheric pressure (FIG. 1). Similar to previous studies, the catalysts were activated under flowing $O_2$ at 823 K, cooled to reaction temperature, purged with helium (He) for 1 h, and contacted with a pure $CH_4$ stream for 0.5 h. However, unlike previous studies using only $H_2O$ for extraction, we hydrolyzed surface-bound methoxy species by flowing a gas mixture comprised of 3.2 kPa of $H_2O$, 0.0025 kPa of $O_2$ and balance $CH_4$. Under these conditions, Cu—Na—ZSM-5 (Cu/Al=0.37, Na/Al=0.26) and Cu—H-ZSM-5 (Cu/Al=0.31) evolved 37 μmol $g_{cat}^{-1}$ and 82 μmol $g_{cat}^{-1}$ of stoichiometric $CH_3OH$, respectively. These values are more than two times higher than those obtained with Cu—Na-ZSM-5 using only He, $O_2$ and $H_2O$ as the extracting gas (9.6 μmol $g_{cat}^{-1}$) or those reported by Lobo et. al. (16 μmol $g_{cat}^{-1}$) using 3.2 kPa $H_2O$ in $N_2$ at 473 K and Schoonheydt et. al. (8 μmol $g_{cat}^{-1}$) using a 50% v/v acetonitrile aqueous solution for 1 h at 298 K to extract the oxidized products.

Remarkably, sustained $CH_4$ oxidation activity was observed when continuing to feed the $CH_4$, $H_2O$ and $O_2$ gas mixture after all stoichiometric $CH_3OH$ was extracted (FIG. 1). Steady state $CH_3OH$ production rates of 0.88±0.02 μmol $h^{-1}$ $g_{cat}^{-1}$ and 1.81±0.01 μmol $h^{-1}$ $g_{cat}^{-1}$ were measured for Cu—Na-ZSM-5 and Cu—H-ZSM-5, respectively. Over Cu—Na-ZSM-5, $CH_3OH$ was the main product generated (as determined by $^1H$ nuclear magnetic resonance) with a selectivity of 70.6±0.4%, while $CO_2$ was the only byproduct generated at a rate of 0.38±0.02 μmol $h^{-1}$ $g_{cat}^{-1}$. $CO_2$ selectivity did not increase when higher conversions were simulated by introducing $CH_3OH$ as a reagent at identical conditions; although, most of $CH_3OH$ was dehydrated into dimethyl ether in the presence of acid sites at these conditions (>60% yield). Notably, the steady state $CH_3OH$ production rates persisted without apparent deactivation, generating a total of 88 μmol $g_{cat}^{-1}$ over 108 h with Cu—Na-ZSM-5—a value roughly five times higher than that reported for the stoichiometric oxidation over Cu—Na-ZSM-5. Similarly, Cu—H—ZSM-5 generated a total of 491 μmol $g_{cat}^{-1}$ over 288 h—a value ca. 1.4 times larger than the total copper content of the zeolite. The excess $CH_3OH$ produced per copper atom in Cu—H-ZSM-5 coupled with the lack of sustained $CH_3OH$ production in the absence of $CH_4$ in the extracting gas mixture over Cu—Na-ZSM-5 (FIG. 1) are strong evidence that $CH_4$ is oxidized catalytically over $H_2O$-tolerant copper sites.

Catalytic turnover was verified with transient experiments using isotopically labeled molecules coupled with on-line mass spectrometry (MS). $^{13}C$ methoxy species were deposited on the zeolite by flowing $^{13}CH_4$ (16.8 kPa $^{13}CH_4$ [99 atom % $^{13}C$, Sigma-Aldrich] with balance He) over an activated Cu—Na-ZSM-5 sample for 0.5 h at 483 K and then flowing a regular $^{12}CH_4/H_2O/O_2$ gas mixture to extract the methoxy species. Enriched $^{13}CH_3OH$ (m/z=33) was detected in the stoichiometric regime, but unlabeled $^{12}CH_3OH$ was observed in the steady state regime, thus suggesting that new, unlabeled $^{12}C$ methoxy species are formed after the initial $^{13}C$ methoxy species are hydrolyzed. Next, the reaction was allowed to proceed at steady state at a measured rate of 0.88 μmol $CH_3OH$ $h^{-1}$ $g_{cat}^{-1}$ for 21 h (equivalent to the production of 18.5 μmol $g_{cat}^{-1}$ of $^{12}CH_3OH$). At this point, the weight hourly space velocity (WHSV) was reduced from 2400 mL $h^{-1}$ $g_{cat}^{-1}$ to 300 mL $h^{-1}$ $g_{cat}^{-1}$ and the gas mixture was switched to $^{13}CH_4/H_2O/O_2$ for 0.5 h before resuming the flow of the regular, unlabeled gas mixture. This effective pulse of labeled $^{13}CH_4$ resulted in the production of labeled $^{13}CH_3OH$ as evidenced by a detectable pulse of the m/z=33 signal without significantly altering steady state production of $CH_3OH$. Similar $^{13}C$ enrichment profiles were observed for $CO_2$ during both isotope switching experiments. Analogous behavior was observed for similar experiments carried out over Cu—H-ZSM-5. Control experiments using $^{12}CH_4$ to populate the activated catalyst with unlabeled $^{12}C$ methoxy species did not generate a significant amount of $^{13}CH_3OH$ in the stoichiometric or steady state regimes, thereby ruling out artifacts or potential effects arising from natural abundance $^{13}CH_4$ in the unlabeled gas stream. Kinetic measurements on Cu—Na-ZSM-5 at 483 K show first, half, and zero order dependencies with respect to $CH_4$, $H_2O$ and $O_2$, respectively. Importantly, replacing $CH_4$ with $CD_4$ in the extracting gas during steady state operation at a WHSV of 240 mL $h^{-1}$ $g_{cat}^{-1}$ decreased the $CH_3OH$ production rate from 0.090 to 0.055 μmol $h^{-1}$ $g_{cat}^{-1}$. This change corresponds to a kinetic isotope effect (KIE) of 1.6±0.1, thus indicating that C—H abstraction is a kinetically relevant step in the catalytic cycle. Taken together, the data from the transient $^{13}CH_4$ pulse experiments, the reaction rate order dependencies, and the kinetic isotope effect confirm catalytic turnover.

Gas pretreatments were varied to gain insight into the origin of catalytic and stoichiometric sites in Cu—Na-ZSM-5. Specifically, Cu—Na—ZSM-5 samples were subjected to three pretreatments at 873 K prior to regular $CH_4$ oxidation and extraction at 483 K: i) calcination under $O_2$ and then under He (20 ppm $O_2$); ii) calcination under He (20 ppm $O_2$); or iii) calcination under He without $O_2$ (<0.1 ppm). In all cases, stoichiometric $CH_3OH$ production drastically diminished (98-100%) but catalytic $CH_3OH$ production was only moderately affected (0-60%). Treating activated Cu—Na-ZSM-5 with He above 723 K has been shown to eliminate the mono-(μ-oxo) dicupric cores for stoichiometric $CH_4$ oxidation. The absence of the mono-(μ-oxo) dicupric sites during steady-state methane oxidation was confirmed with UV-visible spectroscopic and online gas chromatographic measurements over Cu—Na-ZSM-5 (Cu/Al=0.37). It has previously been observed that a small fraction of $H_2O$-tolerant sites in copper-exchanged mordenite (Cu-MOR) that did not require high temperature reactivation for stoichiometric $CH_4$ oxidation experiments after exposure to $H_2O$. However, in the present study, exposing Cu—Na-ZSM-5 to $H_2O/O_2$/He at 483 K prior to contacting it with $CH_4$ completely eliminated stoichiometric $CH_3OH$ production but did not affect catalytic $CH_3OH$ production. The onset of the catalytic regime was nearly identical for all samples (240 min on-stream) after exposure to $CH_4/H_2O/O_2$ Cu—Na-ZSM-5 pretreated at 823 K first with $O_2$ and then with He (20 ppm $O_2$) shows that catalytic production began after 240 min on-stream despite $H_2O$ breaking through the catalyst bed after 25 min. A comparable induction process was observed when Cu—Na-ZSM-5 was pretreated without $O_2$ and exposed to a $CH_4/H_2O$ gas mixture at 483 K. In this case $CH_3OH$ was detected only ca. 300 min after $O_2$ was introduced into the system. Hydrated copper species are known to weakly associate with the zeolite framework, becoming mobile and easily oxidized. In copper-exchanged zeolites with the chabazite topology (Cu-SSZ-13), hydrated $Cu^{2+}$ ions have been shown to migrate under flowing wet $O_2/N_2$ (and trace NO and $NH_3$) gas mixtures between 403-523 K during the selective catalytic reduction (SCR) of $NO_x$ to form transient dimeric active sites. The strong similarities between the reaction temperature and the gaseous atmosphere ($H_2O/O_2$) used during both the SCR of $NO_x$ and the oxidation of $CH_4$ could imply that mobile, hydrated copper species also rearrange into active sites for catalytic $CH_4$ oxidation as they do for the SCR of $NO_x$.

TABLE 3A

Catalytic $CH_4$ oxidation rates for various zeolite topologies.

| Material | Framework | Channel Size (Å)[28] | Si/Al$_{nom}$[a] | Si/Al$_{tot}$[b] | Cu/Al$_{tot}$[c] | Specific Activity[d] | STY ($h^{-1} \times 10^{-3}$)[e] |
|---|---|---|---|---|---|---|---|
| H—ZSM-5 | MFI | 5.3 × 5.6<br>5.1 × 5.5 | 11.5 | 13.2 | 0.31 | 1.79 ± 0.02 | 5.2 ± 0.05 |
| H-Beta | BEA | 6.6 × 6.7<br>5.6 × 5.6 | 12.5 | 13.3 | 0.30 | 0.80 ± 0.01 | 2.4 ± 0.04 |
| MCM-41 | MCM-41 | 30 | 12 | 16.1 | 0.74 | 0.36 ± 0.02 | 0.6 ± 0.03 |
| H—ZSM-5 | MFI | 5.3 × 5.6<br>5.1 × 5.5 | 11.5 | 13.9 | 0.13 | 0.84 ± 0.02 | 6.0 ± 0.17 |
| H-Mordenite | MOR | 6.5 × 7,<br>2.6 × 5.7 | 10 | 11.1 | 0.14 | 0.84 ± 0.01 | 4.6 ± 0.08 |
| H-Ferrierite | FER | 4.2 × 5.4<br>3.5 × 4.8 | 10 | 10.6 | 0.12 | 0.44 ± 0.01 | 2.7 ± 0.04 |
| Na—ZSM-5 | MFI | 5.3 × 5.6<br>5.1 × 5.5 | 11.5 | 13.6 | 0.37 | 0.88 ± 0.02 | 2.2 ± 0.04 |
| Na—Y | FAU | 7.4 × 7.4 | 5.1 | 4.6 | 0.45 | 0.30 ± 0.01 | 0.3 ± 0.01 |
| Na—SAPO-34 | CHA | 3.8 × 3.8 | 0.3 | 0.6 | 0.02 | 0.84 ± 0.03 | 7.9 ± 0.29 |
| Na—SSZ-13 | CHA | 3.8 × 3.8 | 15 | 13.8 | 0.50 | 3.12 ± 0.01 | 6.1 ± 0.03 |
| CuO$_x$—MFI[f] | MFI | 5.3 × 5.6<br>5.1 × 5.5 | ∞ | ∞ | ∞ | 0 | 0 |
| CuO$_x$—BEA[f] | BEA | 6.6 × 6.7<br>5.6 × 5.6 | ∞ | ∞ | ∞ | 0 | 0 |
| H—ZSM-5[f] | MFI | 5.3 × 5.6<br>5.1 × 5.5 | 11.5 | 12.9 | 0 | 0 | 0 |

Catalyst pretreatment: 5 h at 823 K under flowing $O_2$, cooled to 483 K under $O_2$ flow and then purged under He for 0.5 h. Initial $CH_4$ oxidation: 0.5 h under 2400 mL $h^{-1}$ $g_{cat}^{-1}$ $CH_4$ at 483 K. Reaction conditions: T = 483 K, WHSV = 2400 mL $h^{-1}$ $g_{cat}^{-1}$, $P_{CH4}$ = 98.1 kPa, $P_{H2O}$ = 3.2 kPa, $P_{O2}$ = 0.0025 kPa (25 ppm).
[a]Si/Al$_{nom}$ denotes the nominal silicon to aluminum ratio in the zeolite based on commercial figures or ratios of $SiO_2$ to $Al_2O_3$ in synthesis procedures.
[b]Si/Al$_{tot}$ denotes the ratio of silicon to aluminum atoms ratio within the zeolite calculated using data from inductively coupled plasma mass spectrometry (ICP-MS) measurements.
[c]Cu/Al$_{tot}$ denotes the ratio of copper to aluminum atoms within the zeolite calculated using ICP-MS.
[d]Specific activity = μmol$_{CH3OH}$ $h^{-1}$ $g_{cat}^{-1}$.
[e]Site time yield (STY) defined as mol $CH_3OH$ (mol Cu)$^{-1}$ $h^{-1}$.
[f]T = 483 K, WHSV = 2400 mL $h^{-1}$ $g_{cat}^{-1}$, $P_{CH4}$ = 93.1 kPa, $P_{H2O}$ = 3.2 kPa, $P_{O2}$ = 0.051 kPa.
The ± symbol denotes 95% confidence intervals.

irrespective of the pretreatment used. The similarity of catalytic rates and onset of $CH_3OH$ production for all pretreated Cu—Na-ZSM-5 samples implies the catalytic sites are different from those responsible for stoichiometric $CH_4$ oxidation, and the catalytic sites are either generated or activated when copper species are exposed to $CH_4$, $H_2O$ and $O_2$ at reaction conditions rather than during the high temperature pretreatment.

An induction period preceding the onset of catalytic $CH_4$ oxidation suggests that copper speciation changes under reaction conditions. The $CH_3OH$ production profile for a regular $CH_4$ oxidation and extraction experiment using Table 3B includes data regarding the cage shape and size for relevent frameworks.

TABLE 3B

| Material | Framework | Cage Shape | Cage Size (Å)[27] |
|---|---|---|---|
| Na—Y | FAU | Spherical | 9.6 × 9.6 |
| Na—SAPO-34 | CHA | Ellipsoidal | 9.4 × 9.4 × 12.7 |
| Na—SSZ-13 | CHA | Ellipsoidal | 9.4 × 9.4 × 12.7 |

Catalytic $CH_4$ oxidation was investigated as a function of the copper content and Brønsted acidity of the zeolite (see Table 4). A control experiment with H-ZSM-5 (Si/Al=11.5) not subjected to copper exchange did not generate $CH_3OH$, thereby confirming that trace transition metal impurities in the zeolite are not responsible for catalytic behavior. Higher Cu/Al ratios in Cu—Na-ZSM-5 and Cu—H-ZSM-5 increased the steady state specific activity (defined as $\mu mol_{MeOH}$ $h^{-1}$ $g_{cat}^{-1}$), but decreased the site-time yield (STY, defined as $mol_{CH3OH}$ $mol_{Cu}^{-1}$ $h^{-1}$), suggesting that the number of active sites does not increase proportionally with the total amount of copper. The presence of Brønsted acid sites increased specific activity and STY for all samples with similar Cu/Al ratios. Indeed, different apparent activation energies ($E_a^{app}$) were observed between the sodium and proton forms of Cu-ZSM-5 (Table 4). Density functional theory calculations over Cu-ZSM-5 have shown that Brønsted acid sites change the energetics of the formation of mono-(μ-oxo) dicupric cores with NO. While mono-(μ-oxo) dicupric cores are likely not present under reaction conditions for catalytic $CH_4$ oxidation, Brønsted acid sites could impart similar changes in the energetics of formation of the catalytic sites.

The catalytic rates and $E_a^{app}$ values of $CH_4$ oxidation are heavily influenced by zeolite topology (see Table 3, Table 4). Cu-MOR, featuring 12-membered ring (MR) pores intersected by sinusoidal 8-MR pores, exhibited either comparable or lower activity at 483 K than that of Cu—H-ZSM-5 (Table 4). However, a significantly higher $E_a^{app}$ of 149 kJ/mol resulted in higher $CH_3OH$ rates at temperatures above 483 K when compared to those of Cu—H-ZSM-5. These results suggest the site speciation and reaction environment within MOR may play a role in stabilizing kinetically relevant transition states. Other topologies, including ferrierite (FER), beta (BEA), Y (FAU) and caged-based SSZ-13 and SAPO-34 (CHA) also oxidize $CH_4$ into $CH_3OH$ but with different rates than those of ZSM-5. Zeolites with large pores at high Cu/Al (0.30-0.50) including BEA (12-MR, 6.6×6.7 Å and 5.6×5.6 Å) and FAU (7.4×7.4 Å windows) showed 50% and 70% lower overall activity when compared to MFI. MCM-41, an amorphous aluminosilicate with large pores of 30 Å, had nearly an order of magnitude lower STY than ZSM-5, indicating that a crystalline, microporous structure with small pores is preferable for catalytic $CH_4$ oxidation. At low Cu/Al (0.12-0.14), Cu—H—ZSM-5 has the highest specific activity and STY (Table 3), while FER (intersecting 10-MR [4.2×5.4 Å] and 8-MR [3.5×4.8 Å]) was half as active as ZSM-5. While Cu-ZSM-5 had the highest specific activity and STY compared to the small-pore zeolites tested, the cage-based aluminoslicate SSZ-13 and the silicoaluminophosphate SAPO-34 with the CHA topology (8-MR windows of 3.8×3.8 Å, ellipsoidal cages of 9.4×9.4×12.7 Å) featured higher STY of $6.1×10^{-3}$ $h^{-1}$ and $7.9×10^{-3}$ $h^{-1}$, respectively, than those in Cu—Na-ZSM-5 or Cu—H-ZSM-5 at similar Cu/Al ratios (Table 3). These studies indicate the catalytic sites or the kinetically relevant transition states are sensitive to the zeolite topology, with materials featuring small pores or cage-based structures showing enhanced performance when compared to those with large pores.

Taking advantage of the large $E_a^{app}$ for Cu—Na-SSZ-13 (Cu/Al=0.50, 100±2.1 kJ $mol^{-1}$), the reaction temperature was systematically increased to achieve higher catalytic rates. The $CH_3OH$ production rate increased from $2.2×10^{-3}$ to $31.6×10^{-3}$ $mol_{CH3OH}$ $(mol Cu)^{-1}$ $h^{-1}$ when increasing the temperature from 463 to 533 K before a decrease in rates was observed. The large $E_a^{app}$ coupled with the stable $CH_3OH$ production over a wide range of temperature suggest that Cu-SSZ-13 zeolites could be further engineered to enhance further catalytic rates. In summary, copper-exchanged zeolites offer a broad and robust platform for the low temperature, catalytic oxidation of $CH_4$ into $CH_3OH$ using $O_2$.

The nature of the catalytic active sites for $CH_4$ oxidation into $CH_3OH$ over copper-exchanged zeolites is currently unknown. Diffuse reflectance UV-visible spectroscopic measurements show peaks forming at 20,800, 26,800, and 30,000 $cm^{-1}$ during steady-state $CH_3OH$ production, possibly corresponding to copper oxide species generated during reaction.

Fourth Non-Limiting Example

This example provides supporting information for the procedures and results discussed in Example Three.
Materials and Methods
Materials
  Commercial Zeolites.
  Zeolites MOR (mordenite, CBV21A, Si/Al=10), ZSM-5 (MFI, CBV2314, Si/Al=11.5), BEA (beta, CP814E, Si/Al=12.5), FER (ferrierite, CP914C, Si/Al=10), and Y (FAU, CBV100, Si/Al=5.1) were purchased from Zeolyst International. MCM-41 (Aluminosilicate Al-MCM-41, Si/Al=12) was purchased from ACS Materials. All zeolites were in the ammonium form except for Y and MCM-41, which were in the sodium form.
Zeolite Synthesis
  Synthesis of SSZ-13 (CHA):
  sodium hydroxide (99.99%, Sigma-Aldrich) was dissolved in $H_2O$ and mixed with N,N,N-trimethyl-1-adamantanamine hydroxide solution (Ada, 25 wt % in $H_2O$, Sachem) followed by the addition of aluminum hydroxide (80.3 wt % $Al(OH)_3$, SPI Pharma 0250) to obtain a colorless solution. After the addition of colloidal silicon dioxide ($SiO_2$) (Ludox® LS-30), the colorless solution was stirred at room temperature for 2 h. The final composition of the mixture was 0.1 $Na_2O$: 0.033 $Al_2O_3$: 1.0 $SiO_2$: 44 $H_2O$: 0.1 $(Ada)_2O$. This mixture was transferred to a 23-mL Teflon-lined stainless steel autoclave (No. 4749, Parr Instruments) and was then subjected to hydrothermal treatment at 433 K for 4 days in an oven under autogenous pressure and rotation (60 rpm). After hydrothermal treatment, the product was separated from the mother liquor by centrifugation, washed several times with distilled $H_2O$, and dried at 393 K. SSZ-13 samples were calcined under dry air (Dry Size 300, Airgas) with the following temperature profile: heat 1 K $min^{-1}$ to 423 K and hold for 2 h at 423 K, then heat 1 K $min^{-1}$ to 623 K and hold for 2 h at 623 K, and lastly heat 1 K $min^{-1}$ to 853 K and hold for 10 h.
  Synthesis of SAPO-34 (CHA):
  Aluminum oxide ($Al_2O_3$) (Catapal® B) and colloidal silicon dioxide ($SiO_2$) (Ludox® AS-40) were added to a mixture of phosphoric acid (85 wt %, Sigma-Aldrich) and $H_2O$. Diethylamine (DEA, 99.5%, Sigma-Aldrich) was added to the mixture to obtain a gel with the composition of $0.8P_2O_5:Al_2O_3:0.6SiO_2:50H_2O:2$ DEA. The mixture was stirred for 0.5 h and then subjected to hydrothermal treatment at 423 K for 7 days with 60 rpm rotation. After hydrothermal treatment, the product was separated from the mother liquor by centrifugation, washed several times with distilled $H_2O$, and dried at 393 K. SAPO-34 samples were calcined under dry air (Dry Size 300, Airgas) with the same temperature profile stated for SSZ-13 samples.

Synthesis of Pure Silica Beta:

Si-BEA was synthesized. Aqueous tetraethylammonium hydroxide (27.169 g, 35 wt % in H$_2$O, Sigma-Aldrich) and tetraethyl orthosilicate (24.160 g, 99%, Sigma Aldrich) were added to a Teflon [polytetrafluoroethylene (PTFE)] dish and stirred at 250 rpm at room temperature for 90 min. Deionized H$_2$O (15 mL) was added and the solution was left uncovered on the stir plate for 12 h to reach a total mass of 33.046 g after evaporation of ethanol and some of the H$_2$O. Next, hydrofluoric acid (2.627 g, 48 wt % in H$_2$O, >99.99% trace metals basis, Sigma-Aldrich) was added drop wise and mixed using a PTFE spatula, resulting in a thick gel. Additional H$_2$O was added to aid homogenization and the sol-gel was allowed to evaporate to 33.848 g. The final molar composition was 1 SiO$_2$:0.56 TEAOH:0.56HF: 7.5H$_2$O. The gel was transferred to a 45 mL PTFE-lined stainless steel autoclave and heated to 413 K for 7-20 days under static conditions. The product was separated from the mother liquor by filtration, washed with distilled H$_2$O, and dried at 373 K. The zeolite was calcined under dry air (Dry Size 300, Airgas) with the same temperature profile stated for SSZ-13 samples.

Synthesis of Pure Silica MFI:

Si-MFI was synthesized. Aqueous tetrapropylammonium hydroxide (12.00 g, 1.0 M in H$_2$O, Sigma-Aldrich) and tetraethyl orthosilicate (5.00 g, 99%, Sigma-Aldrich) were added to a Teflon [polytetrafluoroethylene (PTFE)] dish and stirred at 300 rpm at room temperature for 60 min. The molar composition was 1SiO$_2$:0.5 TPAOH:22H$_2$O. The gel was transferred to a 23 mL PTFE-lined stainless steel autoclave and heated to 453 K for 2 days under static conditions. The product was separated from the mother liquor by centrifugation, washed with distilled H$_2$O, and dried at 373 K. The zeolite was calcined under dry air (Dry Size 300, Airgas) with the same temperature profile stated for SSZ-13 samples.

Ion Exchange

Sodium Exchange.

The following procedure was used to ion-exchange all zeolites: 1 g of zeolite was stirred in 36 mL of 2.44 M sodium acetate (>99%, Sigma-Aldrich) at 353 K for 4 h. Zeolites were subsequently filtered while hot and rinsed with 120 mL of deionized H$_2$O. Zeolites were then dried for 4 h at 393 K in a drying oven. The above procedure was repeated three times.

Copper Exchange.

The following procedure was used to ion-exchange all zeolites: 1 g of zeolite was stirred in 60 mL of 0.001-0.05 M solutions of copper (II) acetate monohydrate (>99%, Sigma-Aldrich) at room temperature overnight. The suspension was then filtered at room temperature and rinsed with 300 mL of deionized H$_2$O. The zeolite was dried overnight at 393 K in a drying oven and subsequently calcined under dry air (Dry Size 300, Airgas) at 823 K for 5 h with a heating ramp of 1 K min$^{-1}$.

Incipient Wetness Impregnation

CuO$_x$-BEA.

0.23 g of a 0.23 M solution of copper (II) nitrate trihydrate (>99%, Sigma-Aldrich) was added dropwise to 0.30 g of Si-BEA under vigorous stirring, yielding 1.1 wt % of CuO$_x$ on the BEA zeolite. CuO$_x$—BEA was dried overnight at 383 K and then calcined at 853 K for 10 h under flowing dry air (Dry Size 300, Airgas) with a heating ramp of 1 K min$^{-1}$. The resultant zeolite had a gray color.

CuO$_x$-MFI.

0.239 g of a 0.241 M solution of copper (II) nitrate was added dropwise to 0.352 g of Si-MFI under vigorous stirring, yielding 1.1 wt % of CuO$_x$ on the MFI zeolite. CuO$_x$-MFI was dried overnight and calcined in the same way as stated for CuO$_x$-BEA. The resultant zeolite had a gray color.

Characterization

Elemental Analysis.

Copper (Cu), sodium (Na), aluminum (Al), and iron (Fe) contents were determined using inductively coupled plasma mass spectrometry (ICP-MS) (Agilent 7900). 2.0-10.0 mg of zeolite were placed in a polyethylene microfuge tube (1.5 mL) and digested in 0.1 mL hydrofluoric acid (48 wt %, trace metals basis, Sigma-Aldrich) for 3 h. The hydrofluoric acid solution was diluted to a total mass of 10.0 g using 2 wt % aqueous nitric acid (HNO$_3$) (veritas purity, GFS Chemicals). 0.10 g of this solution was then added to two solutions: 1) 0.10 g of 1 part per million (ppm) erbium in 2 wt % HNO$_3$ solution; 2) 9.80 g of 2 wt % HNO$_3$. The final concentration of each element was 10 parts per billion (ppb) erbium and between 10 to 300 ppb for Cu, Na, Al, and Fe. A five point calibration curve was built using the following ICP standard solutions: 1,000 ppm Cu in 2 wt % HNO$_3$, 1,000 ppm Al in 2 wt % HNO$_3$, 1,000 ppm Na in 2 wt % HNO$_3$, and 1,000 ppm Fe in 2 wt % HNO$_3$. All standard solutions were purchased from Sigma-Aldrich (TraceCERT).

Calculations of Molar Ratios Si/Al$_{tot}$ and Cu/Al$_{tot}$.

The unit cell of a zeolite is given by:

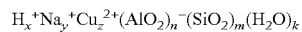

where subscripts refer to the molar ratios of each component within the unit cell of a zeolite. Local charge balance was assumed to occur within the zeolite, requiring x=n−2z−y.

From the unit cell given above, the mass balance of the unit cell is given by the following equation on a per gram zeolite basis:

$$1 = a\frac{\text{g SiO}_2}{\text{g zeolite}} + b\frac{\text{g [AlO}_2]^-}{\text{g zeolite}} + c\frac{\text{g Cu}^{2+}}{\text{g zeolite}} + d\frac{\text{g Na}^+}{\text{g zeolite}} + e\frac{\text{g H}^+}{\text{g zeolite}} + f\frac{\text{g H}_2\text{O}}{\text{g zeolite}}$$

where each coefficient represents the weight percent of each species. The weight percent of Al, Cu, and Na were directly calculated using ICP-MS, allowing b, c, and d to be determined. Converting the weight percentages of Al, Cu, and Na to mole percentages per gram zeolite, e was then calculated using the local charge balance of cations on the zeolite framework. The weight percentage of H$_2$O (f) was assumed to be equal to the weight percentage of H$_2$O in the zeolite framework unit cell (2-7 wt %). The mass balance was then solved for the weight percentage of SiO$_2$ (a).

Si/Al$_{tot}$ was calculated by $$\frac{\text{Si}}{\text{Al}_{tot}} = \frac{a}{b}\frac{m_{AlO_2}}{m_{SiO_2}} \times \frac{1 \text{ mol Si}}{1 \text{ mol SiO}_2} \times \frac{1 \text{ mol AlO}_2}{1 \text{ mol Al}}$$

where m$_i$ is the molar mass of element i.

Cu/Al$_{tot}$ was calculated by $$\frac{\text{Cu}}{\text{Al}_{tot}} = \frac{c}{b}\frac{m_{AlO_2}}{m_{Cu}} \times \frac{1 \text{ mol AlO}_2}{1 \text{ mol Al}}$$

Powder X-Ray Diffraction.

The crystal structures of zeolite catalysts were determined from powder x-ray diffraction patterns collected using a Bruker D8 diffractometer using Cu-Kα radiation (λ=1.5418 Å, 40 kV, 40 mA). Data were recorded in the range of 3-50 2θ with an angular step size of 0.02° and a counting time of 0.068 s per step.

Surface Area and Pore Volume Quantification.

Nitrogen adsorption and desorption isotherms were measured on a Quantachrome Autosorb iQ apparatus at liquid nitrogen temperature (77 K). Prior to the adsorption analysis, all samples were pelletized and degassed under vacuum for 12 h at 623 K. Micropore volume and total pore volume were determined from the amount of $N_2$ adsorbed at $P/P_0=0.01$ and $P/P_0=0.95$, respectively.

Transmission Electron Microscopy (TEM).

Transmission electron microscopy was performed on a JEOL 2010F equipped with a field emission gun (FEG) operating at 200 kV. Magnifications of obtained images ranged from 50,000× to 100,000×.

Coupled In-Situ UV-Vis-NIR Spectroscopy and Online Gas Chromatography.

UV-Vis spectroscopy was performed on a Cary 5000 UV-Vis-NIR spectrometer (Agilent Technologies) equipped with a DiffusIR diffuse reflectance accessory (PIKE Technologies) and environmental chamber (HTV, PIKE Technologies) with a quartz window. Absolute reflectance was measured from 11,000 $cm^{-1}$ to 52,600 $cm^{-1}$ with a scan rate of 11,700 $cm^{-1}$ $min^{-1}$. All spectra were normalized with respect to background spectra of hydrated Na-ZSM-5. The gas outlet from the environmental temperature chamber was connected to a gas chromatograph (Agilent Technologies, model 6890N) equipped with an S-bond column (Restek Rt-S-bond, 30 m, 0.25 mm ID, #19770) and flame ionization detector. The oven temperature was isothermal at 373 K for 10 min.

To conduct in-situ $CH_4$ oxidation reactions, the temperature was controlled using a PIKE PC Controlled Temperature Module. Cu-ZSM-5 (Cu/Al=0.37) was ground into a fine powder before loading 10.0 mg into the sample cell. The flow of gases, including He (ultra high purity, Airgas), $O_2$ (ultra high purity, Airgas), 1% $O_2$/He (ultra high purity, Airgas), and $CH_4$ (research grade, Airgas) were controlled with independent mass flow controllers (Brooks Instruments LLC). $H_2O$ (typically 3.2 kPa) was introduced into the gas stream using a saturator maintained at 298 K.

Catalytic $CH_4$ Oxidation Reactions $CH_4$ oxidation reactions were conducted in a continuous, tubular flow reactor (stainless steel tube, O.D. 12.5 mm, wall thickness=0.889 mm). The reactor tube was mounted inside of a single-zone furnace (850 W/115V, Applied Test Systems Series 3210). Temperature was controlled using a thermocouple (Omega, model TJ36-CASS-18U) mounted slightly downstream of the catalyst bed connected to a temperature controller (Digi-Sense model 68900-10). 2.0 g of zeolite particles (pelletized and sieved into 500-1000 μm particles) were packed between quartz wool plugs and rested on the thermocouple in the middle of the furnace heating zone. The flow of gases, including He (ultra high purity, Airgas), $O_2$ (ultra high purity, Airgas), 1% $O_2$ in $N_2$ (ultra high purity, Airgas), and $CH_4$ (research grade, Airgas) were controlled with independent mass flow controllers (Brooks Instruments LLC). $H_2O$ (typically 3.2 kPa) was introduced into the gas stream using saturator maintained at 298 K. $O_2$ partial pressure entering the catalyst bed was monitored with an $O_2$ sensor (3000-G-115BTP, Omega Instruments) placed at the entrance of the furnace. Prior to reaction, the zeolite was usually calcined in situ under 50 mL $min^{-1}$ flowing $O_2$ for 5 h at 823 K and cooled under flowing $O_2$ to reaction temperature (473-498 K). Upon reaching reaction temperature, the zeolite was purged under 50 mL $min^{-1}$ of He for 0.5 h. The gas flow was then changed to 80 mL $min^{-1}$ $CH_4$ for 0.5 h followed by 80 mL $min^{-1}$ of $CH_4$, $H_2O$, and $O_2$ (typically 98.1 kPa, 3.2 kPa, and 0.0025 kPa respectively). $CH_3OH$ partial pressures evolved during catalytic $CH_4$ oxidation were quantified using a gas chromatograph (Agilent Technologies, model 6890N) equipped with an S-bond column (Restek Rt-S-bond, 30 m, 0.25 mm ID, #19770) and flame ionization detector. The oven temperature was isothermal at 373 K for 30 min.

Simulated high conversion $CH_4$ oxidation experiments were performed in the same reactor described above. Catalyst activation was the same as described above. Liquid reactants $CH_3OH$ and $H_2O$ were introduced into the gas stream via saturators maintained at 273 K and 298 K respectively. The reaction mixture of 0.70 kPa $CH_3OH$, 2.25 kPa $H_2O$, and variable $O_2$ partial pressure was attained by combining two gas streams at the inlet of the reactor: 1) 15 mL $min^{-1}$ He directed through $CH_3OH$ contained in a saturator, and 2) 65 mL $min^{-1}$ total of 1% $O_2$ in He and/or He gas streams directed through $H_2O$ contained in a saturator. $CH_3OH$, dimethyl ether, $CO_2$, and $H_2O$ were monitored using a gas chromatograph (Agilent Technologies, model 6890N) equipped with thermal conductivity detector and a Carboxen 1006 PLOT column (Sigma-Aldrich, 30 m, 0.32 mm ID, #24241-U). The oven temperature profile was initially 313 K for 2 min, then ramped 10 K $min^{-1}$ to 393 K, and then isothermal for 15 min.

Product Quantification.

Calibration curves for $CH_3OH$ were constructed using a known vapor pressure of $CH_3OH$ taken into a $CH_4$ stream. $CH_3OH$ vapor pressure was controlled by immersing the saturator containing $CH_3OH$ into cooling baths at several temperatures (e.g. ice water at 273 K, dry ice in ethanol at 201 K, etc). Relative response factors were calculated using the gas chromatograph between known $CH_4$ and $CH_3OH$ partial pressures. Calibration curves for $CO_2$ were constructed by flowing known mixtures of 1% $CO_2$/helium and helium to a gas chromatograph-mass spectrometer.

The following definitions were used to quantify experimental data:

The large partial pressure of $CH_4$ in the gas stream during catalytic $CH_4$ oxidation reactions prevented the accurate quantification of $CH_4$ consumption. As such, $CH_4$ conversion was assumed to be equal to the total molar flow rate of carbon of all observed products divided by the initial molar flow rate of $CH_4$:

$$X_{CH4} = \frac{\sum_{i=1}^{N} C_i F_i}{F_{CH4,0}}$$

where $X_{CH4}$ is the conversion of $CH_4$, $F_i$ is the molar flow rate of product i, $C_i$ is the number of carbon atoms in product i, $\Sigma\, C_i F_i$ is the total molar flow rate of carbon of all products, and $F_{CH4,0}$ is the initial molar flow rate of $CH_4$.

As explained above, the amount of $CH_4$ consumed was not quantifiable. Thus, product selectivity for catalytic $CH_4$ oxidation was defined as:

$$S_i = \frac{C_i F_i}{\sum_{i=1}^{N} C_i F_i}$$

where $S_i$ is the selectivity of product i, $C_i$ is the number of carbon atoms in product i, $F_i$ is the molar flow rate of product i, and $\Sigma C_i F_i$ is the total molar flow rate of carbon of all products.

For CH$_3$OH oxidation experiments, CH$_3$OH conversion was defined as:

$$X_{CH3OH} = 1 - \frac{F_{CH3OH}}{F_{CH3OH,0}}$$

where $X_{CH3OH}$ is the conversion of CH$_3$OH, $F_{CH3OH}$ is the molar flow rate of CH$_3$OH at steady state, and $F_{CH3OH,0}$ is the initial molar flow rate of CH$_3$OH.

Product selectivity was defined as:

$$S_i = \frac{C_i F_i}{F_{CH3OH,0} - F_{CH3OH}}$$

where $S_i$ is the product selectivity, $C_i$ is the carbon number for product i, $F_i$ is the molar flow rate of product i, and $F_{CH3OH,0} - F_{CH3OH}$ is the molar flow rate of CH$_3$OH reacted at steady state.

Product yield was defined as:

$$Y_i = \frac{C_i F_i}{F_{CH3OH,0}}$$

where $Y_i$ was the yield for product i, $F_i$ is the steady state molar flow rate of product i, is the number of carbon atoms in product i, and $F_{CH3OH,0}$ is the initial molar flow rate of CH$_3$OH.

Transient Experiments with Isotopically Labelled Molecules.

The isotopically labeled experiments were performed in the reactor setup described in the introduction to the Catalytic CH$_4$ oxidation reactions subsection. $^{13}$C-methoxy species were deposited on the zeolite surface by exposing a freshly activated zeolite to 50 mL min$^{-1}$ of 17% $^{13}$CH$_4$/He (using $^{13}$CH$_4$ [99 atom % $^{13}$C, Sigma Aldrich]) for 0.5 h. $^{13}$C-methoxy species were extracted with a mixture of $^{12}$CH$_4$/H$_2$O/O$_2$ (98.1/3.2/0.0025 kPa). $^{13}$CH$_4$ pulses were introduced by flowing a 3.2 kPa H$_2$O, 0.0025 kPa O$_2$, and balance $^{13}$CH$_4$ gas mixture at a flow rate of 10 mL min$^{-1}$ for 0.5 h before resuming a flow of 3.2 kPa H$_2$O, 0.0025 kPa O$_2$, and $^{12}$CH$_4$ balance. CH$_3$OH and CO$_2$ isotopes were analyzed using a gas chromatograph (Agilent Technologies, model 7890N) equipped with a quadrupole mass spectrometer and an S-bond column (Restek Rt-S-bond, 30 m, 0.25 mm ID, #19770). The oven temperature profile was isothermal at 373 K for 30 min. $^{13}$CO$_2$ was tracked with m/z=45. $^{13}$CH$_3$OH was monitored using m/z=33 instead of 32 because of small O$_2$ leaks into the gas chromatograph-mass spectrometer. O$_2$ leaks elevated the m/z=32 signal and prevented the detection of trace $^{13}$CH$_3$OH signals relative to background O$_2$. However, m/z=33 did not interfere with O$_2$.

Section S1: Product Identification for CH$_4$ Oxidation Over Cu—Na-ZSM-5 (Cu/Al=0.37)

Cu—Na-ZSM-5 was activated under oxygen (O$_2$) for 5 h at 823 K, cooled to reaction temperature at 483 K under flowing O$_2$, and then purged under helium (He) for 1 h. After reaction with methane (CH$_4$) for 0.5 h, an extraction gas of 3.2 kPa of water (H$_2$O), 0.0025 kPa O$_2$ and CH$_4$ balance was flowed over the Cu—Na-ZSM-5 bed. A steady state methanol (CH$_3$OH) rate of 0.88 μmol h$^{-1}$ g$_{cat}^{-1}$ was achieved after 10 h on-stream. A condenser was placed in-line downstream from the catalyst bed. Next, the gas stream containing CH$_4$/H$_2$O/O$_2$ and the oxidation products was passed through the condenser maintained at 201 K in a dry ice-ethanol bath. After 6 h on-stream, the frozen products were thawed in D$_2$O, removed from the in-line condenser, and injected into a quartz nuclear magnetic resonance (NMR) tube (528-PP-7, Wilmad LabGlass) for analysis. $^1$H-NMR performed on the condensate in a 500 MHz spectrometer (Varian Inova-500) showed CH$_3$OH as the only product. Gas phase products of the reactor effluent were analyzed using a gas chromatograph equipped with a quadrupole mass spectrometer (Agilent 7890N). The only gas phase product from the reaction was carbon dioxide (CO$_2$). Assuming CO$_2$ and CH$_3$OH were the only reaction products, the steady state CH$_4$ conversion was 0.0014% and the CH$_3$OH selectivity was 70.6%. The conditions resulting in the data shown in FIG. 2 is as follows: Catalyst pretreatment: 5 h at 823 K under flowing O$_2$, cooled to 483 K under O$_2$ flow and then purged under He for 0.5 h. Initial CH$_4$ oxidation: 0.5 h under 2400 mL h$^{-1}$ g$_{cat}^{-1}$ of CH$_4$ at 483 K. Reaction conditions: T=483 K, WHSV=2400 mL h$^{-1}$ g$_{cat}^{-1}$, P$_{CH4}$=98.1 kPa, P$_{H2O}$=3.2 kPa, P$_{O2}$=0.0025 kPa (25 ppm). (■) CH$_3$OH partial pressure (kPa). (○) CO$_2$ partial pressure (kPa). (◇) CH$_3$OH selectivity.

Section S2: Simulation of High Conversion CH$_4$ Oxidation Via CH$_3$OH Oxidation Over Cu—Na-ZSM-5 (Cu/Al=0.37)

The over-oxidation of CH$_3$OH into CO$_2$ at higher CH$_4$ conversion levels was simulated by introducing CH$_3$OH as a reactant. The direct oxidation of CH$_4$ into CH$_3$OH over copper-exchanged ZSM-5 under regular conditions generated a conversion of 0.0014%. At these conditions, the low O$_2$ partial pressure (0.0025 kPa) was sufficient to convert CH$_4$ into CH$_3$OH (4.5×10$^4$ kPa O$_2$ is needed to produce CH$_3$OH at a rate of 0.88 μmol h$^{-1}$ g$_{cat}^{-1}$), but it was observed that the excess O$_2$ further oxidized CH$_3$OH into CO$_2$ at 483 K (30% selectivity to CO$_2$). Therefore, since higher conversion of CH$_4$ (e.g. 1%) will require more O$_2$ in the reaction mixture, the excess O$_2$ at this scale could also over-oxidize CH$_3$OH into CO$_2$ decreasing the overall selectivity of the process.

To evaluate CO$_2$ selectivity at higher CH$_4$ conversions, CH$_3$OH was used as a reactant to simulate the gas composition the Cu—Na-ZSM-5 (Cu/Al=0.37) catalyst bed would encounter at 100% CH$_4$ conversion. After activating Cu—Na-ZSM-5 for 5 h at 823 K under O$_2$, the zeolite bed was cooled to 483 K and purged under He for 1 h. Then a reaction mixture of 0.70 kPa CH$_3$OH, variable O$_2$ partial pressure, 2.25 kPa H$_2$O and He was passed over the catalyst bed. Flowing this reaction mixture over Cu—Na-ZSM-5 and measuring the extent of CO$_2$ production can be used as a surrogate to calculate the maximum CO$_2$ selectivity. A 0.70 kPa partial pressure of CH$_3$OH simulated a CH$_4$ partial pressure of 0.70 kPa being fully converted into CH$_3$OH. The O$_2$ partial pressure was varied to represent unreacted or excess O$_2$ from a typical CH$_4$ oxidation experiment. Helium (He) was used instead of CH$_4$ in the gas mixture to isolate CH$_3$OH oxidation and exclude the coadsorption of CH$_4$ on the zeolite surface. The gas mixture composed of 0.70 kPa CH$_3$OH, 2.25 kPa H$_2$O, and O$_2$ was flowed over the Cu—Na-ZSM-5 catalyst for 5 h at 483 K before the steady state gas composition was analyzed in order to allow for changes in copper speciation that occur in regular CH$_4$ oxidation experiments. As the O$_2$ partial pressure was increased from 0.21 kPa to 2.70 kPa, the CO$_2$ yield increased from 6.8% to 24%. The rate order of O$_2$ in CH$_3$OH oxidation was ca. 0.50. As expected, lower amounts of O$_2$ relative to CH$_3$OH (lower O$_2$/CH$_3$OH partial pressure ratio) suppress the formation of CO$_2$. However, even having up to 4 times the partial pressure of O$_2$ as CH$_3$OH only generated a 24% yield and 25% selectivity of CO$_2$, which was a lower CO$_2$ selectivity than that observed during regular CH$_4$ oxidation experiments over Cu—Na-ZSM-5 at similar conditions. Therefore, these results suggest that CH$_4$ oxidation to higher conversions will not result in a substantial increase in $CO_2$ production or a decrease in $CH_3OH$ selectivity at 483 K.

$CO_2$ selectivity could be further reduced by lowering the temperature of the simulated gas mixture over Cu—Na-ZSM-5. As the reaction temperature was lowered to 463 K, the $CO_2$ yield and selectivity decreased from 24% to 7.4%. These data show that $CH_3OH$ selectivity could increase beyond 70% by lowering the reaction temperature (<483 K) in a high conversion $CH_4$ oxidation process.

$CH_3OH$ conversion was greater than 90% for the simulated, high conversion $CH_4$ oxidation experiments where the vast majority of $CH_3OH$ was converted into dimethyl ether (DME) (>60% yield). DME is produced from the acid-catalyzed dehydration of $CH_3OH$. Brønsted acid sites in zeolites are well known to perform this reaction between 473 and 573 K. However, zeolites can still produce DME even with trace Bronsted acidity, such as that present in sodium-exchanged ZSM-5. $CH_3OH$ dehydration is thermodynamically favorable under the $CH_3OH$ oxidation reaction conditions of 483 K, 0.70 kPa $CH_3OH$, and 2.25 kPa $H_2O$. The reaction $2\ CH_3OH \leftrightarrow (CH_3)_2O + H_2O$ has a chemical equilibrium constant ($K_{eq}$) of 14.8 under these reaction conditions, and the equilibrium conversion of $CH_3OH$ to DME would be 92%.

In the simulated, high conversion $CH_4$ oxidation experiments, the DME yield decreased from 80% to 62% as the $O_2$ partial pressure increased from 0.21 kPa to 2.7 kPa, consistent with $CH_3OH$ or DME being oxidized into $CO_2$. At a lower temperature of 463 K, the DME yield increased from 62% to 74%.

DME was not observed in typical $CH_4$ oxidation experiments over Cu—Na-ZSM-5 due to the low equilibrium conversion of $CH_3OH$ into DME. At steady state, taking the $CH_3OH$ partial pressure to be $10^{-3}$ kPa and the $H_2O$ partial pressure to be 3.2 kPa, the equilibrium conversion of $CH_3OH$ into DME at 483 K would be 0.90%. The theoretical maximum amount of DME that could be produced was below the detection limit of the gas chromatograph used to quantify steady state rates.

Section S5: $^{13}CO_2$ Production During Transient, Isotopically Labelled Experiments Over Cu—Na-ZSM-5 (Cu/Al=0.37)

$^{13}C$ methoxy species were deposited on the zeolite by flowing $^{13}CH_4$ (16.8 kPa $^{13}CH_4$ [99 atom % $^{13}C$, Sigma-Aldrich] with balance He) over activated Cu—Na-ZSM-5 for 0.5 h at 483 K and then using a regular $^{12}CH_4/H_2O/O_2$ gas mixture to evolve oxidation products from the zeolite. Enriched $^{13}CO_2$ (m/z=45) is quickly produced in the stoichiometric regime, but unlabeled $^{12}CO_2$ is observed in the steady state regime, thus suggesting unlabeled $^{12}C$ surface species are oxidized into $^{12}CO_2$ once the $^{13}C$ species are depleted. The reaction rate remained at steady state (rate=0.88 $\mu mol_{CH3OH}\ h^{-1}\ g_{cat}^{-1}$) for 21 h at a weight hourly space velocity (WHSV) of 2400 mL $h^{-1}\ g_{cat}^{-1}$ (equivalent to the production of 18.5 $\mu mol\ g_{cat}^{-1}$ of $12CH_3OH$). Next, the gas mixture was switched to $^{13}CH_4/H_2O/O_2$ for 0.5 h at a WHSV=300 mL $h^{-1}\ g_{cat}^{-1}$ before resuming the flow of the regular, unlabeled mixture. This $^{13}CH_4$ pulse resulted in the production of $^{13}CO_2$ during steady state $CH_3OH$ production. Control experiments using $^{12}CH_4$ to populate the activated catalyst with unlabeled $^{12}C$ methoxy species did not generate a significant amount of $^{13}CO_2$ in the stoichiometric or steady state regimes.

Section S6: Isotopically Labelled Experiments Over Cu—H-ZSM-5 (Cu/Al=0.31)

Catalytic turnover was also verified over Cu—H-ZSM-5 (Cu/Al=0.31). When an activated Cu—H-ZSM-5 was reacted with $^{13}CH_4$ before extraction, a large pulse of $^{13}CH_3OH$ was observed in the stoichiometric regime. However, as $CH_3OH$ production approached steady state, $^{13}CH_3OH$ production declined and resulted in the production of exclusively $^{12}CH_3OH$. However, virtually no $^{13}CH_3OH$ was extracted from the zeolite when $^{12}CH_4$ was used for the initial reaction. These experiments show that the source carbon for $CH_3OH$ produced at steady state must come from gas phase $^{12}CH_4$, thereby indicating turnover on the Cu—H-ZSM-5 surface.

Section S7: Kinetic Order Dependence of Reactants and Transient, Isotopic Pulsing of $CD_4$ Over Cu—Na-ZSM-5 (Cu/Al=0.37)

The partial pressure of $O_2$ was varied over Cu—Na-ZSM-5 (Cu/Al=0.37, Na/Al=0.26) to deduce the order of $O_2$ on catalytic $CH_4$ oxidation activity. After activating the zeolite under $O_2$ at 823 K for 5 h, Cu—Na—ZSM-5 was cooled to 483 K under $O_2$ flow, purged under He, and reacted under dry 75% $CH_4/He$ at 483 K for 0.5 h. Afterwards, 3.2 kPa $H_2O$ and $O_2$ were then introduced into the reactant stream. The $O_2$ partial pressure was controlled using a 1% $O_2/N_2$ gas stream co-fed with He while maintaining $CH_4$ and $H_2O$ partial pressures at 72.5 kPa and 3.2 kPa respectively. As the partial pressure of $O_2$ decreased, the observed catalytic $CH_3OH$ production rate remained fairly constant, showing the rate was zero order with respect to $O_2$.

The catalytic $CH_3OH$ production rate demonstrated positive kinetic orders with respect to $CH_4$ and $H_2O$ partial pressures. The rate dependence of $CH_4$ was investigated by varying $CH_4$ partial pressure from 49 to 98 kPa while maintaining $H_2O$ and $O_2$ partial pressures constant at 3.2 kPa and 0.0025 kPa respectively. The catalytic rate of $CH_3OH$ production exhibited a first order dependence on $CH_4$ partial pressure, indicating the dilution of $CH_4$ in the reaction feed is undesired. Similarly, $H_2O$ increased the production of $CH_3OH$ from Cu—Na-ZSM-5. $H_2O$ vapor pressure was controlled between 1.1 to 3.2 kPa using aqueous $CaCl_2$ solutions in a saturator maintained at 298 K. The $CH_4$ and $O_2$ partial pressures were kept constant at 98 and 0.0025 kPa respectively. $CH_3OH$ production decreased as the $H_2O$ partial pressure decreased by order of 0.5. As expected, when no $H_2O$ was delivered to the catalyst, no $CH_3OH$ was detected, indicating that $H_2O$ was necessary for $CH_3OH$ extraction.

Section S9: In-Situ Diffuse Reflectance UV-Visible Spectroscopy and Online Gas Chromatography Measurements Over Cu—Na-ZSM-5 (Cu/Al=0.37)

UV-visible spectroscopic and online gas chromatographic measurements were performed over Cu—Na-ZSM-5 (Cu/Al=0.37) to gain insight into copper speciation during pre-treatments and steady-state operation. The zeolite was heated at 5 K/min under flowing $O_2$ to 823 K and then calcined under He (20 ppm $O_2$) at 823 K for 2 h. A shoulder at 22,700 $cm^{-1}$ decayed within 1 h of He treatment, indicating the majority of the mono-(µ-oxo) dicupric cores were eliminated. Cu—Na-ZSM-5 was then cooled to 483 K under He and then exposed to pure $CH_4$ for 0.5 h. No significant changes in the UV-visible spectra were observed, further suggesting the elimination of most of the mono-(µ-oxo) dicupric cores. After flowing 93.2 kPa CH4, 0.051 kPa $O_2$, and 3.2 kPa $H_2O$ at 483 K, a small amount of stoichiometric $CH_3OH$ was extracted from zeolite before steady-state $CH_3OH$ production, consistent with kinetic experiments. During stoichiometric $CH_3OH$ production, there were no changes in the 22,700 $cm^{-1}$ region. Lastly, no bands were present at 22,700 $cm^{-1}$ peak during steady-state $CH_3OH$ production, indicating the mono-(µ-oxo) dicupric cores are likely not present during catalytic operation.

Section S10: Catalytic $CH_4$ Oxidation Over Cu-ZSM-5 and Cu-MOR Zeolites

TABLE 4

$CH_4$ oxidation over Cu-exchanged ZSM-5 and MOR zeolites

| Material | Framework | $Si/Al_{nom}{}^a$ | Co-Cation | $Si/Al_{tot}{}^b$ | $Cu/Al_{tot}{}^c$ | Specific Activity$^d$ | STY$^e$ (×10$^{-3}$ h$^{-1}$) | $E_a{}^{app\,f}$ (kJ/mol) |
|---|---|---|---|---|---|---|---|---|
| ZSM-5 | MFI | 11.5 | Na$^+$ | 13.1 | 0.17 | 0.51 | 2.7 | 47 ± 2 |
| | | | | 13.6 | 0.37 | 0.88 | 2.2 | 54 ± 5 |
| | | | H$^+$ | 13.9 | 0.13 | 0.84 | 6.0 | 88 ± 6 |
| | | | | 14.1 | 0.38 | 1.51 | 3.8 | 80 ± 2 |
| Mordenite | MOR | 10 | Na$^+$ | 11.4 | 0.14 | 0.30 | 1.8 | 92 ± 3 |
| | | | H$^+$ | 11.1 | 0.14 | 0.84 | 4.6 | 149 ± 2 |

Catalyst pretreatment: 5 h at 823 K under flowing $O_2$, cooled to 483 K under $O_2$ flow and then purged under He for 0.5 h. Initial $CH_4$ oxidation: 0.5 h under 2400 mL h$^{-1}$ g$_{cat}{}^{-1}$ $CH_4$. Reaction conditions: T = 483 K, WHSV = 2400 mL h$^{-1}$ g$_{cat}{}^{-1}$, $P_{CH4}$ = 98.1 kPa, $P_{H2O}$ = 3.2 kPa, $P_{O2}$ = 0.0025 kPa (25 ppm). ± denotes 95% confidence intervals
$^a$nominal ratio of silicon to aluminum atoms in each zeolite based on commercial figures.
$^b$ratio of total silicon to aluminum atoms in each zeolite sample. Determined using inductively coupled plasma mass spectrometry (ICP-MS).
$^c$ratio of total copper to aluminum atoms in each zeolite sample. Determined using ICP-MS.
$^d$specific activity is defined as $\mu mol_{CH3OH}$ h$^{-1}$ g$_{cat}{}^{-1}$.
$^e$Site-time yield (STY) is defined as mol $CH_3OH$ (mol Cu)$^{-1}$ h$^{-1}$.
$^f$ $E_a{}^{app}$ is defined as apparent activation energy (kJ/mol).

Section S13: Materials Characterization

TABLE 5

Elemental composition, pore volume and surface area analysis (BET) of Cu-exchanged zeolites

| Material$^a$ | Framework | Si/Al$^b$ | Si/Al$_{tot}{}^c$ | Cu/Al$^d$ | Cu wt %$^e$ | Fe/Al$^f$ | $V_{micro}$ (cm$^3$ g$_{cat}{}^{-1}$)$^g$ |
|---|---|---|---|---|---|---|---|
| Na—ZSM-5 | MFI | 11.5 | 13.6 | 0.37 | 2.5 | 0.01 | 0.14 |
| Na—ZSM-5 | MFI | 11.5 | 13.1 | 0.17 | 1.2 | 0.01 | 0.14 |
| H-ZSM-5 | MFI | 11.5 | 13.2 | 0.31 | 2.2 | 0.01 | 0.14 |
| H-ZSM-5 | MFI | 11.5 | 13.9 | 0.13 | 0.9 | 0.01 | 0.15 |
| H-ZSM-5 | MFI | 11.5 | 12.9 | 0 | 0 | 0.01 | 0.16 |
| Na—MOR | MOR | 10 | 11.4 | 0.14 | 1.1 | 0.01 | 0.17 |
| H-MOR | MOR | 10 | 11.1 | 0.14 | 1.1 | 0.01 | 0.19 |
| H-MOR | MOR | 10 | 10.4 | 0 | 0 | 0.00 | 0.20 |
| Na—SSZ-13 | CHA | 15 | 13.8 | 0.50 | 3.3 | 0.00 | 0.24 |

$^a$zeolite material with parent counter cation form before copper-exchange. Na denotes sodium form, H denotes proton form.
$^b$nominal ratio of total silicon to aluminum atoms in the zeolite based on commercial figures or ratios of $SiO_2$ to $Al_2O_3$ in synthesis procedures.
$^c$calculated ratio of total silicon to aluminum atoms in the zeolite. Quantified using inductively coupled plasma mass spectrometry (ICP-MS).
$^d$calculated ratio of total copper to aluminum atoms in copper-exchanged zeolite. Quantified using ICP-MS.
$^e$weight percent of copper in copper-exchanged zeolite.
$^f$calculated ratio of total iron to aluminum atoms in copper-exchanged zeolite. Quantified using ICP-MS. Fe/Al was quantified to provide an estimate of iron impurities in copper-exchanged zeolites.
$^g$micropore volume of copper-exchanged zeolites determined by BET analysis.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of catalytically forming an alcohol from an alkane, comprising:
exposing a catalyst to an atmosphere comprising the alkane, an oxidizing agent, and a protic solvent, wherein the catalyst is exposed to the alkane, the oxidizing agent, and the protic solvent simultaneously, and wherein alcohol is formed by conversion of the alkane, the oxidizing agent, and the protic solvent.

2. A method of catalytically forming methanol from methane, comprising:
exposing a catalyst to an atmosphere comprising methane, oxygen, and water, wherein the catalyst is exposed to the methane, the oxygen, and water simultaneously, and wherein methanol is formed by conversion of methane, oxygen, and water.

3. A method of catalytically forming methanol from methane, comprising:
exposing a catalyst to methane, oxygen, and water, wherein methanol is formed by conversion of methane, oxygen, and water at a steady state production rate of from about 0.5 to about 160 μmol per hour per gram of catalyst.

4. The method of claim 1, wherein the alkane comprises methane and the alcohol comprises methanol.

5. The method of claim 1, wherein the oxidizing agent comprises oxygen ($O_2$).

6. The method of claim 1, wherein the protic solvent comprises water.

7. The method of claim 3, wherein the catalyst is exposed to methane, oxygen, and water simultaneously.

8. The method of claim 1, wherein the step of exposing is carried out at a temperature between about 190° C. and about 400° C.

9. The method of claim 1, wherein a selectivity of the reaction for methanol is at least 70%.

10. The method of claim 1, wherein the catalyst comprises a zeolite.

11. The method of claim 10, wherein the zeolite is associated with a counter cation comprising a metal.

12. The method of claim 11, wherein the metal comprises copper.

13. The method of claim 10, wherein the zeolite comprises a framework selected from the group consisting of ZSM-5, mordenite (MOR), ferrierite (FER), beta (BEA), and chabazite (CHA).

14. The method of claim 10, wherein the zeolite comprises a silicoaluminophosphate.

15. The method of claim 1, wherein water is present in the atmosphere at a partial pressure of from about 0.1 kPa to about 5 kPa during the exposing step.

16. The method of claim 15, wherein oxygen is present in the atmosphere at a partial pressure of from about 0.0001 kPa to about 0.1 kPa during the exposing step.

17. The method of claim 16, wherein the balance of the atmosphere is methane during the exposing step.

18. The method of claim 1, wherein a number of moles of methane generated for the duration of steady state operation exceeds a number of moles of active sites of the catalyst.

19. The method of claim 1, wherein a number of moles of methane generated for the duration of steady state operation exceeds a number of moles of counter cation in the catalyst.

20. The method of claim 1, wherein the alcohol is formed by conversion of the alkane, the oxidizing agent, and the protic solvent to the alcohol in a reactor, into which the alkane, the oxidizing agent, and the protic solvent are introduced and from which the alcohol exits.

21. The method of claim 10, wherein the zeolite comprises a framework selected from the group consisting of AEI and AFX.

22. The method of claim 10, wherein the counter cation comprises a combination of copper and another metal.

23. The method of claim 10, wherein the counter cation comprises a combination of sodium and copper or zinc and copper.

24. The method of claim 2, wherein the catalyst comprises a zeolite.

25. The method of claim 24, wherein the zeolite is associated with a counter cation comprising a metal.

26. The method of claim 3, wherein the catalyst comprises a zeolite.

27. The method of claim 26, wherein the zeolite is associated with a counter cation comprising a metal.

* * * * *

UNITED STATES PATENT AND TRADEMARK OFFICE
CERTIFICATE OF CORRECTION

PATENT NO. : 10,099,979 B2  
APPLICATION NO. : 15/329628  
DATED : October 16, 2018  
INVENTOR(S) : Yuriy Román-Leshkov et al.

Page 1 of 1

It is certified that error appears in the above-identified patent and that said Letters Patent is hereby corrected as shown below:

On the Title Page

The Applicants, Inventors, and Assignees should be listed as follows:
(71) Applicants: Massachusetts Institute of Technology, Cambridge, MA (US);
ExxonMobil Research and Engineering Company, Annandale, NJ (US)

(72) Inventors: Yuriy Román-Leshkov, Cambridge, MA (US);
Karthik Narsimhan, Cambridge, MA (US);
Randall J. Meyer, Clinton, NJ (US);
Pedro M. Serna Merino, Branchburg, NJ (US)

(73) Assignees: Massachusetts Institute of Technology, Cambridge, MA (US);
ExxonMobil Research and Engineering Company, Annandale, NJ (US)

Signed and Sealed this  
Twelfth Day of March, 2019

Andrei Iancu  
*Director of the United States Patent and Trademark Office*